United States Patent [19]

Iwamoto et al.

[11] Patent Number: 5,359,085

[45] Date of Patent: Oct. 25, 1994

[54] FULGIMIDE DERIVATIVES

[75] Inventors: Osamu Iwamoto, Ikeda; Taizo Hara, Ibaraki; Haruhiko Sugiyama, Shiga, all of Japan

[73] Assignee: Wako Pure Chemical Industries, Ltd., Osaka, Japan

[21] Appl. No.: 558,549

[22] Filed: Jul. 27, 1990

[30] Foreign Application Priority Data

Jul. 28, 1989 [JP] Japan ............................. 1-195640
Sep. 19, 1989 [JP] Japan ............................. 1-242446

[51] Int. Cl.$^5$ ............... C07D 207/404; C07D 403/06; C07D 407/06; C07D 409/06; C07D 421/06
[52] U.S. Cl. ......................... 548/468; 548/518; 548/525; 548/527; 548/545; 548/546; 548/547
[58] Field of Search ............ 548/545, 546, 468, 518, 548/525, 527, 547

[56] References Cited

U.S. PATENT DOCUMENTS 4,220,708 9/1980 Heller ............................. 430/336

OTHER PUBLICATIONS

Quantum Yields of the Phtochromic Reactions of Heterocyclic Fulgides and Fugimides, by Veerle Deblauwe and Georges Smets, *Makromol. Chem.* 189, pp. 2503–2512, 1988, Belgium.

English Abstract of German Patent No. 2647850, Mar. 2, 1978.

English Abstract of German Patent No. 2441759, Mar. 13, 1975.

*Primary Examiner*—David B. Springer
*Attorney, Agent, or Firm*—Armstrong, Westerman, Hattori, McLeland & Naughton

[57] ABSTRACT

A fulgimide derivative of the formula:

wherein $R^1$, $R^2$, $R^3$ are independently alkyl cycloalkyl aryl etc.; $R^4$ is thienyl, indolyl, furyl, etc.; X is a divalent organic residue; and R is amino, OH, etc., or a vinyl group, has a photochromic action and can be used for producing photochromic polymers and copolymers.

19 Claims, No Drawings

FULGIMIDE DERIVATIVES

BACKGROUND OF THE INVENTION

This invention relates to a fulgimide derivative having photochromic activity and useful as recording and memory materials, copying materials, printed photosensitive bodies, photosensitive materials for laser, photosensitive materials for photo-composing, photosensitive materials for display, etc.

Compounds having properties of producing changes in absorption spectra when exposed to irradiation of ultraviolet light, or visible light of short wavelength, are generally called photochromic compounds. These photochromic compounds are expected to be useful as recording and memory materials, copying materials, printed photosensitive bodies, photosensitive materials for laser, photosensitive materials for photo-composing, photosensitive materials for display, etc. As these photochromic compounds, there are generally well known azobenzenes, viologens, triphenylmethanes, spirobenzopyrans, spironaphthoxazines, fulgides, etc. Among these compounds, spirobenzopyrans and spironaphthoxazines are widely studied now. These compounds form colors when exposed to light, but have a defect in that fading takes place by heat even if stored in the dark. Therefore, these are problems in using these compounds as recording media.

On the other hand, fulgide compounds form a color by exposing such to light of 300 to 400 nm, and the color formed hardly fades by heat but extinguish the color by visible light. Thus, the fulgide compounds have recently been noticed as a photochromic compound useful as a recording medium. The fulgide compounds include fulgide derivatives having a structure of dicarboxylic anhydride and fulgimide derivatives. Among them, the fulgide derivatives have problems in water resistance and heat resistance due to having the structure of dicarboxylic anhydride. Therefore, the fulgimide derivatives are noticed as a recording medium.

The fulgimide derivatives are produced, for example, as follows:

A compound of the formula:

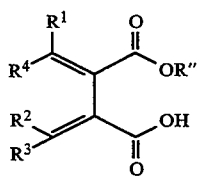

[III']

wherein $R^1$, $R^2$, $R^3$ and $R^4$ are independently a hydrogen atom, a halogen atom, an alkyl group which can have one or more substituents, an alkoxy group, a cycloalkyl group, an aryl group, an aralkyl group or an aryloxy group, or $R^2$ and $R^3$ may be bonded each other to form a ring group such as an adamantyl group, a norbornyl group, etc.; $R^4$ is a group of the formula:

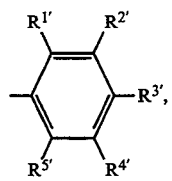

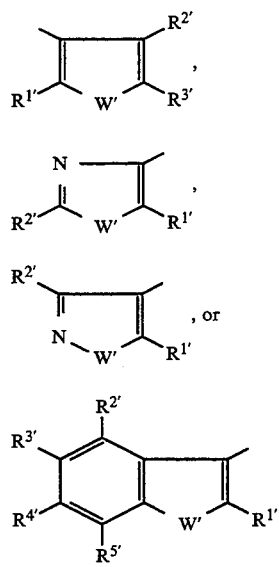

wherein $R^{1'}$ is a hydrogen atom, a halogen atom, an alkyl group or an alkoxy group; $R^{2'}$, $R^{3'}$, $R^{4'}$ and $R^{5'}$ are independently a hydrogen atom, an alkyl group, an alkoxy group, an aryl group, an aralkyl group, an aryloxy group or a halogen atom; $W'$ is an oxygen atom, a sulfur atom, a selenium atom or $=N-R^{6'}$; $R^{6'}$ is a hydrogen atom, an alkyl group, an aralkyl group or an aryl group; $R''$ is an alkyl group, is reacted with

R#NHMgBr wherein $R^\#$ is a hydrogen atom, an alkyl group, an alkoxy group, an aryl group or an aralkyl group, to form a corresponding succinimide acid, followed by reaction with an acid chloride or acid anhydride to yield a fulgimide derivative of the formula:

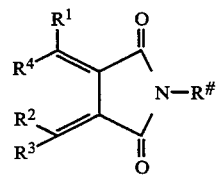

[I']

wherein $R^1$, $R^2$, $R^3$, $R^4$ and $R^\#$ are as defined above (German Offenlegungsschrift 2,441,759 and 2,647,850).

Alternatively, a compound of the formula:

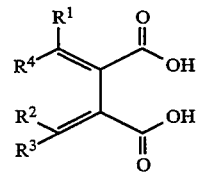

[III]

wherein $R^1$, $R^2$, $R^3$ and $R^4$ are as defined above is reacted with

R#NH₂ wherein $R^\#$ is as defined above, to form a succinimide acid, followed by reaction with an acid chloride or an acid anhydride to yield a fulgimide derivative of the formula [I'] (German Offenlegungsschrift 2,441,759 and 2,647,850).

According to these processes, since an acid chloride or acid anhydride is used in the reaction, it is very difficult to synthesize fulgimide derivatives having a reactive functional group such as an amino group, a hydroxyl group, or the like. Further, it is more difficult to introduce a functional group such as an amino group, a hydroxyl group, or the like into the fulgimide derivative of the formula [I'] thus synthesized.

The fulgimide derivative of the formula [I'] has no reactive functional group, so that its application is limited to i) mixing with a suitable monomer for polymerization and molding, ii) dissolving with a suitable solvent to dye a molded resin therein, and iii) dissolving with a suitable solvent for use as a coating composition, an ink, a dye, etc. Further, articles obtained by coating with a fulgimide derivative of the formula [I'] or mixing a polymer with a fulgimide derivative of the formula [I'], followed by molding, are not only poor in water resistance (release of the fulgimide derivative by washing with water) and chemical resistance, but non-uniform in color formation when exposed to light. Improvement of these defects has long been desired.

SUMMARY OF THE INVENTION

It is an object of the present invention to provide a fulgimide derivative having a photochromic action and useful as recording and memory materials, copying materials, printed photosensitive bodies, photosensitive materials for laser, photosensitive materials for photo-composing, materials for display, etc., and a process for production thereof.

It is another object of the present invention to provide a fulgimide derivative having a vinyl group, and useful as a starting material for producing a polymeric compound having a photochromic action.

The present invention provides a fulgimide derivative of the formula:

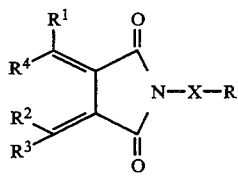
[I]

wherein $R^1$, $R^2$ and $R^3$ are independently a hydrogen atom, a halogen atom, an alkyl group which may have one or more substituents, an alkoxy group, a cycloalkyl group, an aryl group, an aralkyl group or an aryloxy group, and $R^2$ and $R^3$ may be bonded each other to form a ring group; $R^4$ is a group of the formula: $R^4$

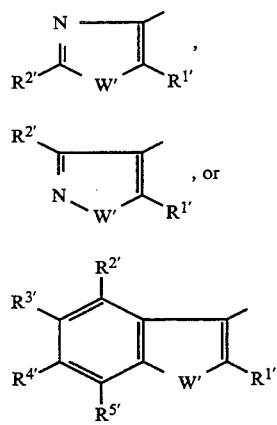

-continued

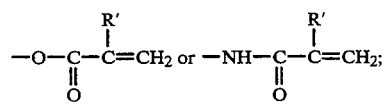

wherein $R^{1'}$ is a hydrogen atom, a halogen atom, an alkyl group or an alkoxy group; $R^{2'}$, $R^{3'}$, $R^{4'}$, and $R^{5'}$ are independently a hydrogen atom, an alkyl group, an alkoxy group, an aryl group, an aralkyl group, an aryloxy group or a halogen atom; $W'$ is an oxygen atom, a sulfur atom, a selenium atom, or $=N-R^{6'}$; $R^{6'}$ is a hydrogen atom, an alkyl group, an aralkyl group or an aryl group; X is a divalent organic residue; R is an amino group which may have one or more substituents, a hydroxyl group, a formyl group, a carboxyl group, a sulfonic acid group, an acetal group, a halogen atom, $$-O-\underset{\underset{O}{\|}}{C}-\underset{R'}{\overset{R'}{C}}=CH_2 \text{ or } -NH-\underset{\underset{O}{\|}}{C}-\underset{R'}{\overset{R'}{C}}=CH_2;$$

alkyl group, or a salt thereof.

The present invention also provide a process for producing a fulgimide derivative of the formula [I] wherein R is an amino group which may have one or more substituents, a hydroxyl group, a formyl group, a carboxyl group, a sulfonic acid group, an acetal group or a halogen atom, which comprises subjecting a compound of the formula:

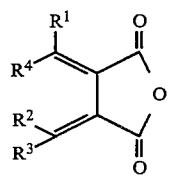
[II]

wherein $R^1$, $R^2$, $R^3$ and $R^4$ are as defined above or a compound of the formula:

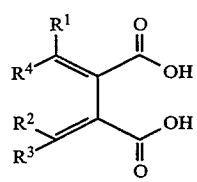
[III]

wherein $R^1$, $R^2$, $R^3$ and $R^4$ are as defined above, or a mixture of a compound of the formula [II] and a com-

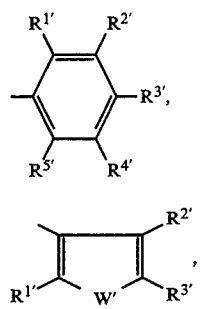

pound of the formula [III], and a compound of the formula:

$$H_2N-X-R \quad [IV]$$

wherein X and R are as defined above, to azeotropic dehydration reaction in a non-polar solvent.

The present invention further provides a process for using a fulgimide derivative of the formula [I], wherein R is $$-O-\underset{\underset{O}{\|}}{C}-\underset{\underset{}{|}}{\overset{R'}{C}}=CH_2 \text{ or } -NH-\underset{\underset{O}{\|}}{C}-\underset{\underset{}{|}}{\overset{R'}{C}}=CH_2;$$

and R' is a hydrogen atom or an alkyl group, as a starting material for producing a polymeric compound having a photochromic action.

DESCRIPTION OF THE PREFERRED EMBODIMENTS

According to the present invention, fulgimide derivatives having a functional group such as an amino group, a hydroxyl group, etc. can be produced easily and effectively. That is, in the reaction of dehydration ring closure of succinimide acid to yield a fulgimide derivative, since a compound of the formula [IV] is used in place of an acid chloride or an acid anhydride and the ring closure is carried out by azeotropic dehydration reaction in a non-polar solvent, a reactive functional group can easily be introduced into the resulting fulgimide derivative. Further, when the resulting fulgimide derivative is reacted with, for example, a compound of the formula:

$$\underset{\underset{}{|}}{\overset{R'}{CH_2=CCO-Z}} \quad [V]$$

wherein Z is a halogen atom such as chlorine, bromine, fluorine, iodine, etc.; and R' is a hydrogen atom or an alkyl group, a fulgimide derivative having a vinyl group can easily be synthesized.

Since the fulgimide derivative of the formula [I] has a functional group, it can be used for producing a polymer of fulgimide derivative, producing a film by the Langmuir-Blodgett (LB) method, fixing a fulgimide derivative to surfaces of various fibers by chemical bonds, etc.

In the compounds of the following formulae [I] to [III]:

[Structure I: fulgimide with $R^1$, $R^4$, $R^2$, $R^3$ substituents and N-X-R]

[Structure II: anhydride form with $R^1$, $R^4$, $R^2$, $R^3$]

[Structure III: diacid form with $R^1$, $R^4$, $R^2$, $R^3$ and two OH groups]

the definitions of the substituents are as follows.

$R^1$, $R^2$ and $R^3$ are independently a hydrogen atom; a halogen atom such as fluorine, chlorine, bromine or iodine; a straight- or branched-chain alkyl group preferably having 1 to 30 carbon atoms such as methyl, ethyl, propyl, butyl, octyl, dodecyl, octadecyl, etc., said alkyl group being able to have one or more substituents such as a hydroxyl group, a straight- or branched-chain alkoxy group such as methoxy, ethoxy, propoxy, butoxy, amyloxy, etc., or a halogen atom such as fluorine, chlorine, bromine or iodine; a straight- or branched-chain lower alkoxy group preferably having 1 to 6 carbon atoms such as methoxy, ethoxy, propoxy, butoxy, etc.; a cycloalkyl group preferably having 3 to 6 carbon atoms such as cyclopropyl, cyclopentyl, cyclohexyl, etc.; an aryl group such as phenyl, tolyl, ethylphenyl, naphthyl, methylnaphthyl, ethylnaphthyl, etc.; an aralkyl group such as benzyl, phenethyl, phenylpropyl, naphthylmethyl, phenylbenzyl, phenylnaphthylmethyl, etc.; an aryloxy group such as phenoxy, methylphenoxy, naphthoxy, phenylphenoxy, phenylnaphthoxy etc. $R^1$, $R^2$ and $R^3$ may be the same or different each other. Further $R^2$ and $R^3$ can be bonded each other to form a ring group such as an adamantyl group, a norbonyl group, etc.

$R^4$ is a group represented by the formula

[Structure: benzene ring with $R^{1'}$, $R^{2'}$, $R^{3'}$, $R^{4'}$, $R^{5'}$]

[Structure: ring with $R^{1'}$, $R^{2'}$, $R^{3'}$, W']

[Structure: N-containing ring with $R^{2'}$, $R^{1'}$, W']

[Structure: N-containing ring with $R^{2'}$, $R^{1'}$, W'] or

-continued

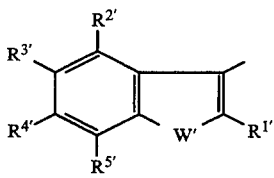

wherein $R^{1'}$ is a hydrogen atom; a halogen atom such as fluorine, chlorine, bromine, or iodine; a straight- or branched-chain lower alkyl group preferably having 1 to 6 carbon atoms such as methyl, ethyl, propyl, butyl, etc.; a straight- or branched-chain lower alkoxy group preferably having 1 to 6 carbon atoms such as methoxy, ethoxy, propoxy, butoxy, etc.; $R^{2'}$, $R^{3'}$, $R^{4'}$ and $R^{5'}$ are independently a hydrogen atom; an alkyl group (either straight- or branched-chain) preferably having 1 to 30 carbon atoms such as methyl, ethyl, propyl, butyl, octyl, dodecyl, octadecyl, etc.; an alkoxy group (either straight- or branched-chain) preferably having 1 to 4 carbon atoms such as methoxy, ethoxy, propoxy, butoxy, etc.; an aryl group such as phenyl, tolyl, ethylphenyl, naphthyl, methylnaphthyl, ethylnaphthyl, etc.; an aralkyl group such as benzyl, phenethyl, phenylpropyl, naphthylmethyl, phenylbenzyl, phenylnaphthylmethyl, etc.; an aryloxy group such as phenoxy, methylphenoxy, naphthoxy, phenylphenoxy, phenylnaphthoxy, etc.; or a halogen atom such as fluorine, chlorine, bromine, or iodine; $R^{2'}$, $R^{3'}$, $R^{4'}$ and $R^{5'}$ may be the same or different each other; and W' is an oxygen atom, a sulfur atom, a selenium atom or $=N-R^{6'}$.

More concretely, in the case of W' being an oxygen atom, $R^4$ is a furyl group, a benzofuryl group, an oxazolyl group or isoxazolyl group; in the case of W' being a sulfur atom, $R^4$ is a thienyl group, a benzothienyl group, or a thiazolyl group; in the case of W' being a selenium atom, $R^4$ is a selenyl group, a benzoselenyl group, etc.; and in the case of W' being $=N-R^{6'}$, $R^4$ is a pyrrolyl group, an indolyl group, an imidazolyl group or a pyrazolyl group. $R^{6'}$ in the $=N-R^{6'}$ group is a hydrogen atom; an alkyl group (either straight- or branched-chain) preferably having 1 to 30 carbon atoms such as methyl, ethyl, propyl, butyl, octyl, dodecyl, octadecyl, etc.; an aryl group such as phenyl, tolyl, ethylphenyl, naphthyl, methylnaphthyl, ethylnaphthyl, etc.; or an aralkyl group such as benzyl, phenethyl, phenylpropyl, naphthylmethyl, phenylbenzyl, phenylnaphthylmethyl, etc.

In the compounds of the formula [I] and the formula:

$$H_2N-X-R \qquad [IV]$$

X is a divalent organic group such as a straight- or branched-chain alkylene group (including a polymethylene group) such as methylene, ethylene, propylene, butylene, amylene, hexylene, heptylene, octylene, nonylene, decylene, undecylene, dodecylene, etc.; an arylene group such as phenylene, methylphenylene, naphthylene, methylnaphthylene, biphenylene, terphenylene, etc.; a group of the formula:

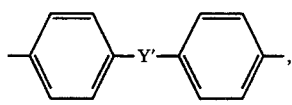

wherein Y' is a straight- or branched-chain alkylene group such as methylene, ethylene, propylene, etc.; a group of the formula:

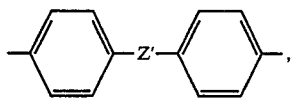

wherein Z' is an oxygen atom, a sulfur atom, or a sulfonyl group; or a cycloalkylene group, e.g. cyclopropylene, cyclopentylene, cyclohexylene, etc.

When X is a group having aromaticity and bonding directly to the N atom of the fulgimide, e.g., a phenylene group, a naphthylene group, a biphenylene group, a terphenylene group,

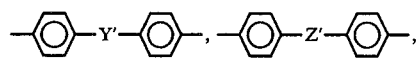

etc., the resulting fulgimide derivatives are more preferable due to having better thermal stability.

R in the formulae [I] and [IV] is an amino group which may have one or more substituents, a hydroxyl group, a formyl group, a carboxyl group, a sulfonic acid group, an acetal group, a halogen atom such as fluorine, chlorine, bromine, or iodine, or a group of the formula:

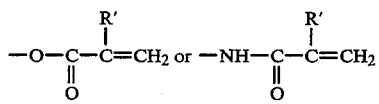

wherein R' is a hydrogen atom or an alkyl group such as methyl, ethyl, propyl, butyl, etc. As the substituents for the amino group, there can be used a straight- or branched-chain alkyl group preferably having 1 to 18 carbon atoms such as methyl, ethyl, propyl, butyl, octyl, dodecyl, octadecyl, etc.; a hydroxyalkyl group such as hydroxyethyl, hydroxypropyl, etc.; sulfoalkyl groups such as sulfopropyl, sulfobutyl etc.; or a straight- or branched-chain acyl group preferably having 2 to 36 carbon atoms such as acetyl, propionyl, butylyl, valeryl, palmitoyl, etc.

When R is an amino group or a substituted amino group, these groups can be in the form of a mineral acid salt such as a hydrochloride, a sulfate, etc., or an organic acid salt such as an acetate, a p-toluenesulfonate, etc. Further, when R is a carboxyl group or a sulfonic acid group, these groups can form a salt together with ammonium or an alkali metal such as lithium, sodium, potassium, etc.

In the formula [I], it is preferable that $R^1$ is a relatively bulky group such as a higher alkyl group or an aryl group. This is because, when $R^1$ is a relatively bulky group, a fulgimide derivative of the formula [I] hardly produces isomers in the color forming reaction by ring closure when the fulgimide derivative is exposed to ultraviolet light.

Preferable examples of the fulgimide derivatives of the formula [I] are as follows.

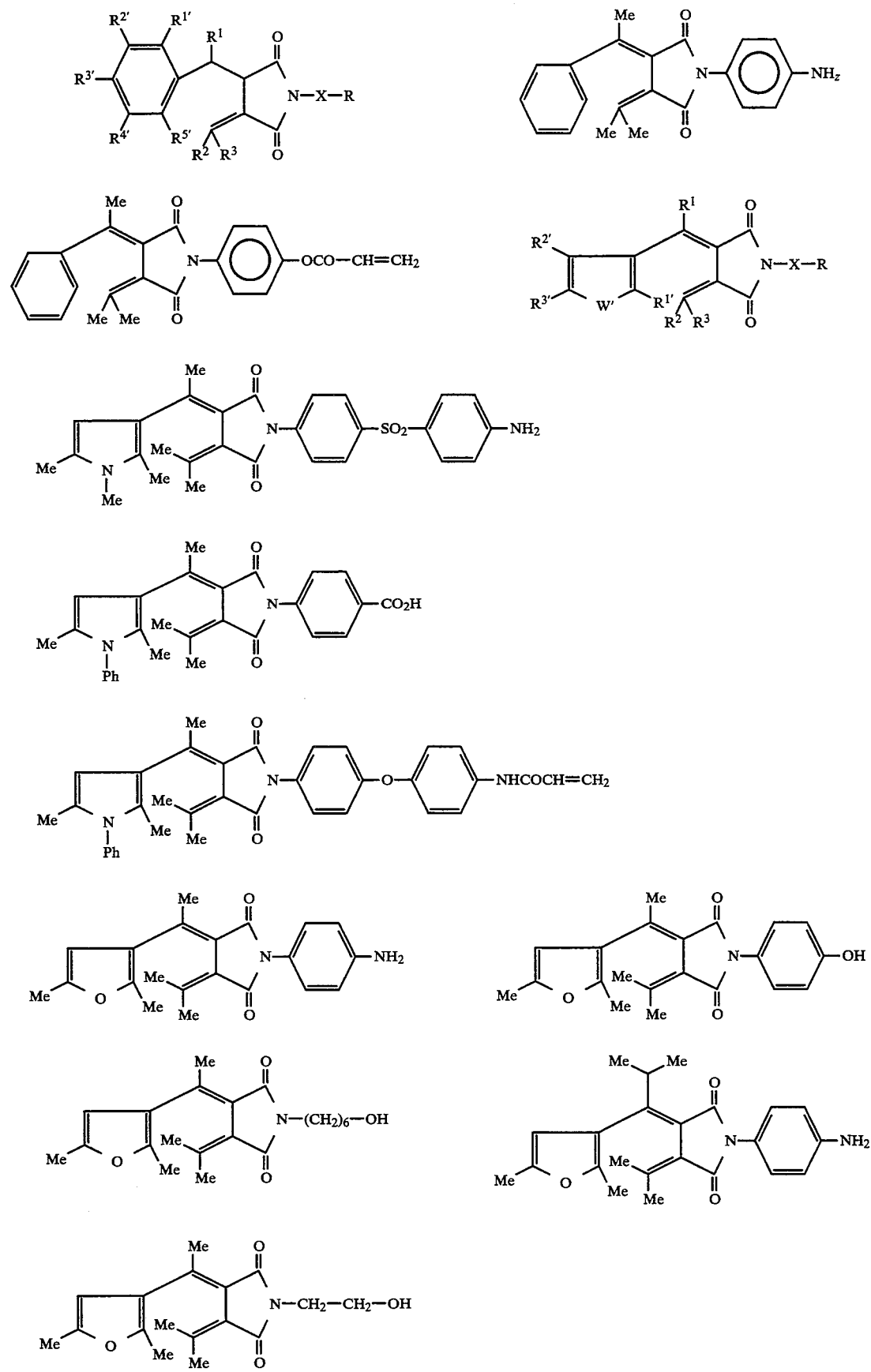

-continued
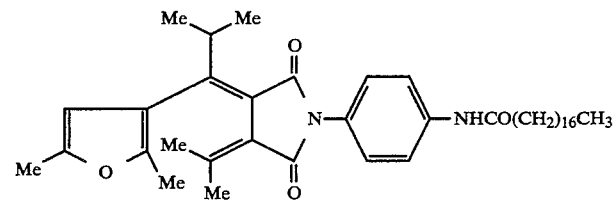
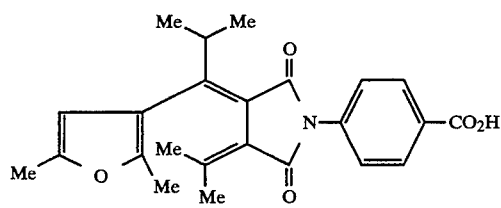
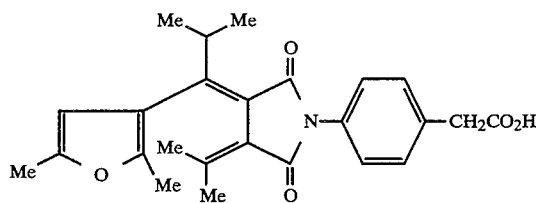
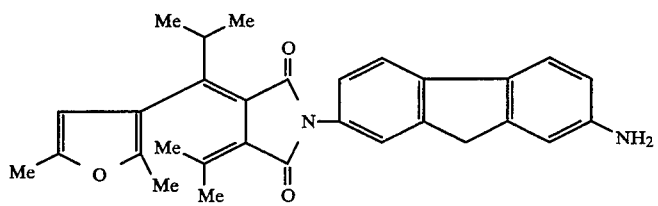
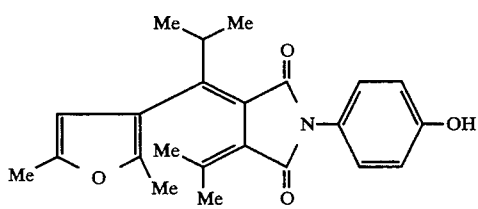
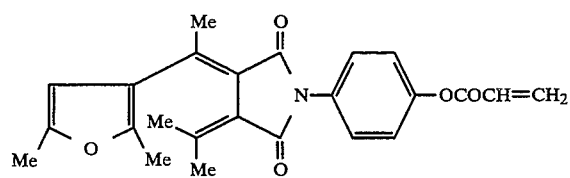
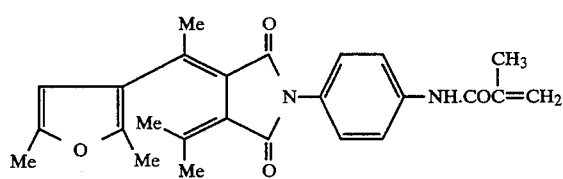
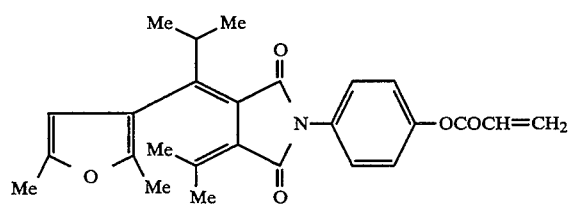
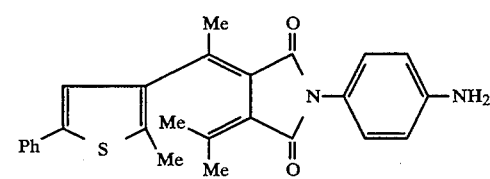
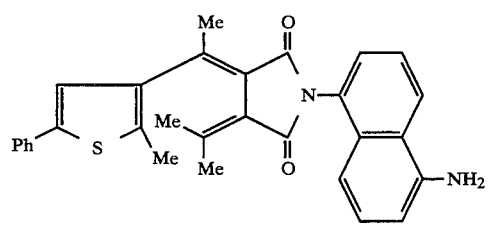
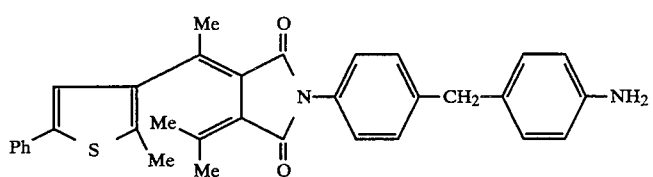
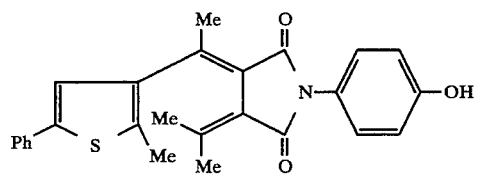
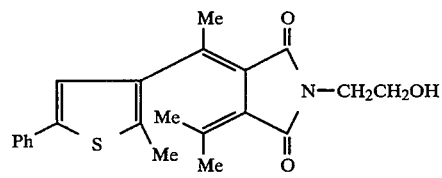

-continued
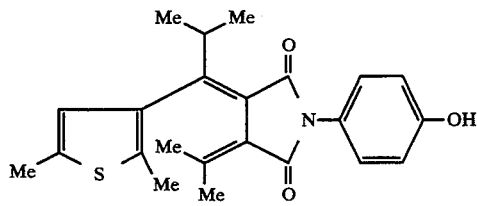
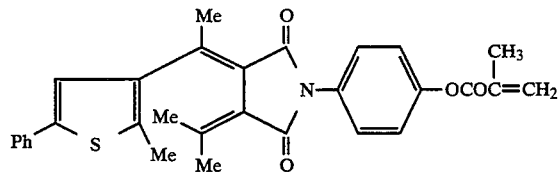
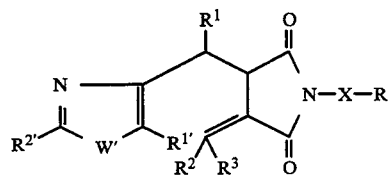
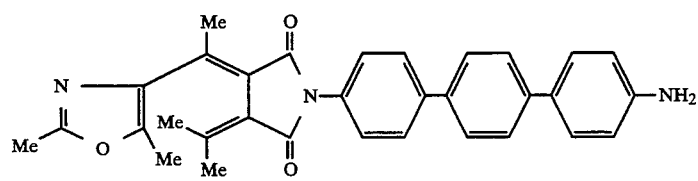
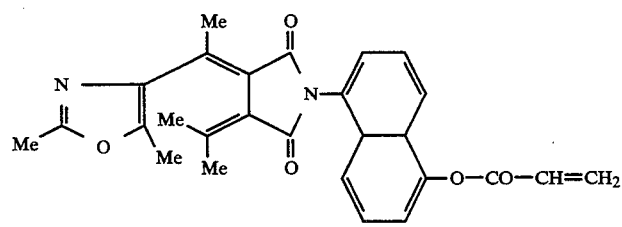
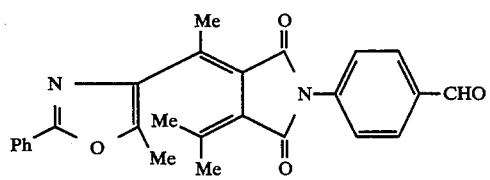
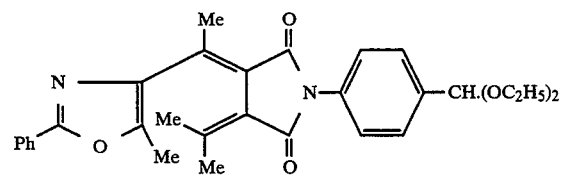
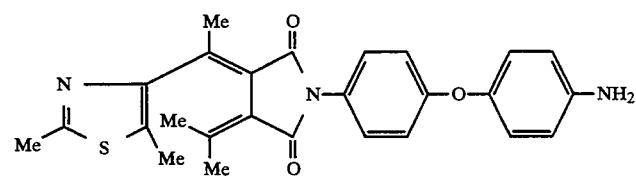
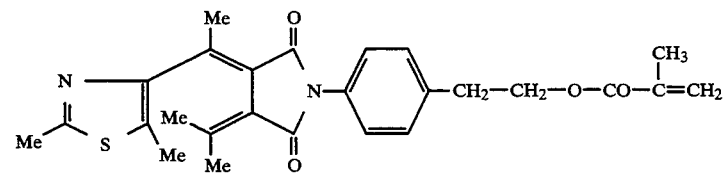
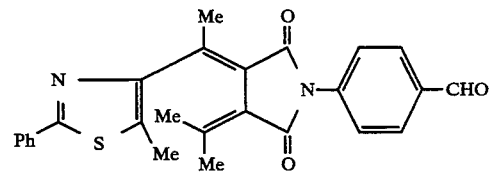
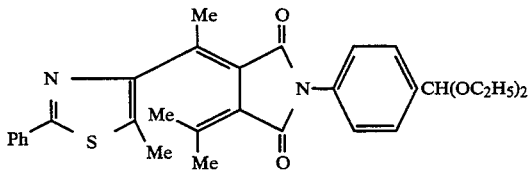

-continued
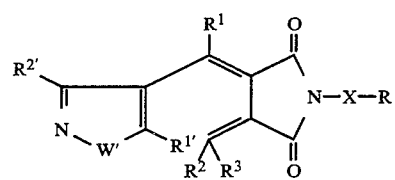
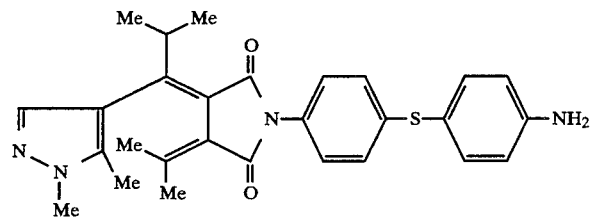
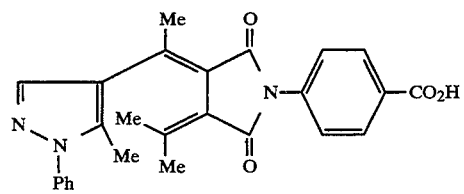
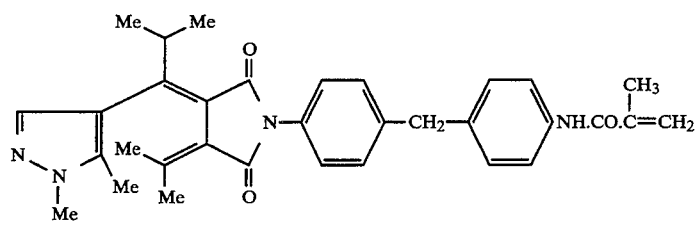
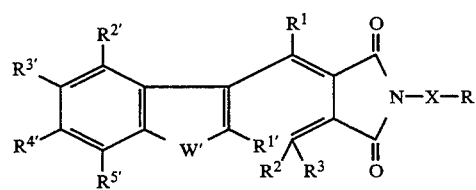
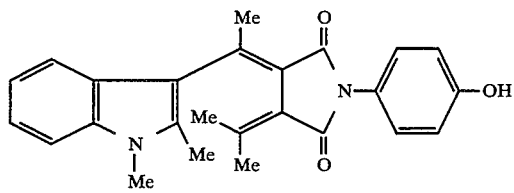
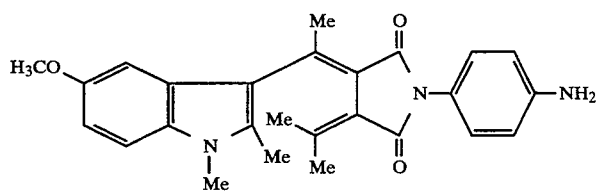
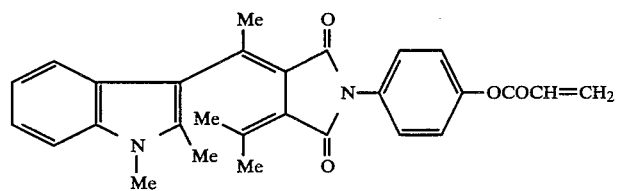
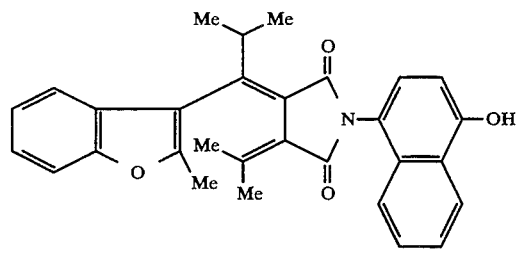
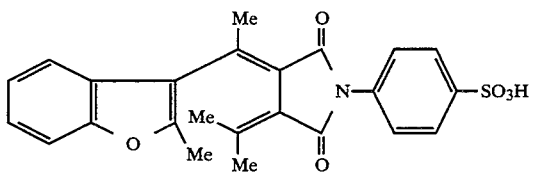

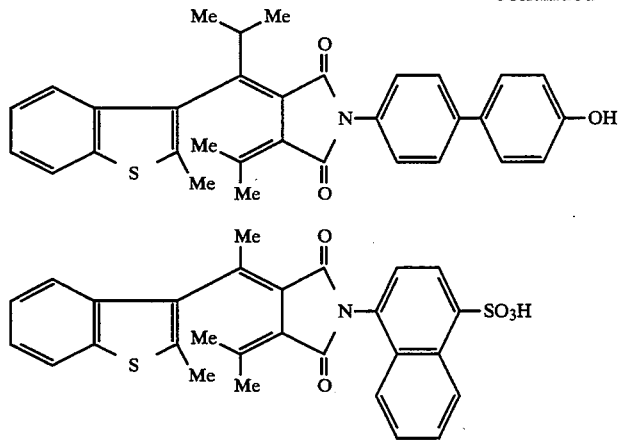

Me = methyl
Ph = phenyl

The fulgimide derivative of the formula [I] can easily be produced by the following processes.

A compound of the formula [II] or a compound of the formula [III] or a mixture thereof in an amount of 1 mole, and 1 mole or more, preferably 1 to 2 moles, of a compound of the formula [IV] are subject to azeotropic dehydration reaction in a non-polar solvent for 1 to 60 hours, preferably 24 to 48 hours to yield a fulgimide derivative of the formula [I-1] wherein R is an amino group which may have one or more substituents, a hydroxyl group, a formyl group, a carboxyl group, a sulfonic acid group, an acetal group or a halogen atom.

As the non-polar solvent, there can be used a solvent having azeotropic properties with water, preferably an aromatic non-polar solvent having azotropic properties with water and a relatively high boiling point. Examples of such non-polar solvent are benzene, toluene, xylene, etc.

The fulgimide derivative of the formula [I-1] is then subjected to purification in a conventional manner, dissolution in a solvent such a benzene, chloroform, dichloromethane, etc., dropwise addition of a compound of the formula [V] in an amount of 1 to 1.2 moles per mole of the compound of the formula [I-1] at 5° C. or lower in the presence of a basic catalyst such as triethylamine, pyridine, etc., and a reaction at near room temperature for 1 to 5 hours to give a fulgimide derivative of the formula [I-2] wherein R is a group of the formula:

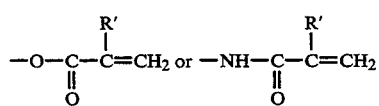

In the above-mentioned reaction, a corresponding acid anhydride or ester can also be used in place of the compound of the formula [V].

The compounds of the formulae [II] and [III] can be produced as follows.

A compound of the formula:

$$R^4-CO-R^1 \quad [VI]$$

wherein $R^1$ and $R^4$ are as defined above, and a compound of the formula:

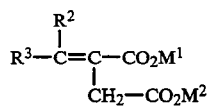

wherein $R^2$ and $R^3$ are as defined above; and $M^1$ and $M^2$ are independently an alkyl group, are subjected to the Stobbe condensation, followed by hydrolysis by a conventional method to give a compound of the formula [III]. The compound of the formula [III] can further be subjected to dehydration reaction using an acid chloride or acid anhydride by a conventional method to yield a compound of the formula [II].

The compound of the formula [VI] can be produced by reacting a compound of the formula:

wherein $R^4$ is as defined above, with a compound of the formula:

$$R^1-COCl$$

wherein $R^1$ is as defined above, and anhydrous aluminum chloride.

The compound of the formula [VII] can be produced by subjecting a dialkyl ester of succinic acid and a compound of the formula:

wherein $R^2$ and $R^3$ are as defined above, to the Stobbe condensation, followed by esterification by a conventional method.

The compound of the formula [IV] is available commercially. It can also be synthesized by a conventional method.

The compound of the formula [V] is available commercially. It can also be synthesized by a conventional method.

The fulgimide derivatives of the formula [I] have a photochromic action and can effectively be used as recording and memory materials, copying materials, printed photosensitive bodies, photosensitive materials for laser, photosensitive materials for photo-composing, photosensitive materials for display, etc. Particularly the fulgimide derivatives of the formula [I-1] wherein R is an amino group which may have one or more substituents, a hydroxyl group, a formyl group, a carboxyl group, a sulfonic acid group, an acetal group or a halogen atom, can effectively used as starting materials for synthesizing fulgimide derivatives further having various useful functional groups, since they have a reactive functional group in their molecules.

The fulgimide derivatives of the formula [I-2] wherein R is a group of the formula:

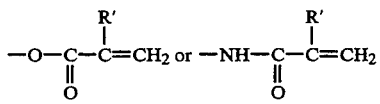

wherein R' is hydrogen or an alkyl group, have a vinyl group in their molecules, so that they can be polymerized by a conventional method, or can be copolymerized with suitable monomers such as acrylic acid, methacrylic acid, acrylic acid ester, methacrylic acid ester, styrene, vinyl acetate, acrylamide, methacrylamide, N,N-dimethylacrylamide, N,N-dimethylmethacrylamide, acrylonitrile, etc. by a conventional method, to give polymeric compounds having photochromic action.

A polymeric compound having photochromic action can be produced from the fulgimide derivative [I-2], for example, as follows.

A compound of the formula [I-2] wherein R is

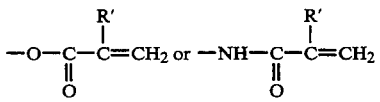

in an amount of 1 mole and 20 to 5000 moles, preferably 30 to 1000 moles of a monomer such as methacrylic acid, methyl methacrylate, etc. are reacted in a solvent such as dimethylformamide in a nitrogen gas stream at 50° to 80° C. for 2 to 10 hours with stirring using a polymerization initiator such as azobisisobutyronitrile.

In the production of a copolymer using a fulgimide derivative of the formula [I-2], it is preferable to select reaction conditions so as to make the content of the fulgimide derivative of the formula [I-2] in an amount of preferably 0.1 to 60 w/w%, more preferably 0.5 to 50 w/w%. When the content of the compound of the formula [I-2] is too low, the color forming ability when exposed to ultraviolet light is insufficient, while when the content is too much, moldability is worsened when processed into various articles by molding, etc.

Various articles can easily be molded using the thus produced polymeric compounds having photochromic action as photochromic materials. Further, the finished articles are excellent in water resistance and chemical resistance, and have an advantage in that the color forming before and after irradiation with light is uniform. Therefore, the polymeric compounds having photochromic action are particularly useful as recording and memory materials.

The present invention is illustrated by way of the following Examples, in which all parts and percents are by weight, unless otherwise specified.

REFERENCE EXAMPLE 1

Synthesis of 2-[(E)-1-(2-methyl-5-phenyl3-thienyl)ethylidene]-3-isopropylidene succinic anhydride (1) Synthesis of 1-phenyl-1,4-pentanedione To 1200 ml of dimethylformamide (DMF) containing 3 moles of benzaldehyde and heated at 35° C., a mixed solution of 0.3 mole of sodium cyanide and 2400 ml of DMF was added dropwise in 30 minutes, and the reaction was carried out for further 30 minutes with stirring. To the reaction solution, a mixed solution of 2.25 moles of methyl vinyl ketone and 2400 ml of DMF was added dropwise in 30 minutes, and the reaction was carried out for further 1 hour. After the reaction, water was poured into the reaction solution, followed by extraction with chloroform. The obtained chloroform solution was washed with dilute sulfuric acid, saturated aqueous solution of sodium bicarbonate, and water in this order, and dried over anhydrous sodium sulfate. The solvent was removed by distillation. The resulting residue was distilled under reduced pressure to give a fraction of pale yellow liquid of 1-phenyl-1,4-pentanedione having a boiling point of 124°–127° C./0.15 mmHg (yield 40%).

(2) Synthesis of 2-methyl-5-phenylthiophene

A mixture of 1 mole of the 1-phenyl-1,4-pentadione obtained in above (1) and 1.1 moles of phosphorus pentoxide was heated to 125°–130° C. and reacted for 1 hour. After the reaction, the objected material was extracted from the reaction solution with ether. The resulting ether solution was washed with a saturated aqueous solution of sodium bicarbonate and water in this order, and dried over anhydrous sodium sulfate. The solvent was removed by distillation. The resulting residue was purified by column chromatography [filler: Wakogel C-300, a trade name, mfd. by Wako Pure Chemical Industries, Ltd.), eluent: a mixed solvent of n-hexane and ethyl acetate] to give yellow crystals of 2-methyl-5-phenylthiophene in yield of 60%, m.p. 49°–51° C.

(3) Synthesis of 3-acetyl-2-methyl-5-phenylthiophene

To a benzene solution containing 1 mole of the 2-methyl-5-phenylthiophene obtained in above (2) and 1 mole of acetic anhydride cooled at 0° C., a benzene solution containing 1 mole of anhydrous stannic chloride was added dropwise in 1.5 hours with stirring. After reacting for further 2 hours with stirring, the reaction solution was poured into 1.5 kg of ice containing 400 ml of 6M HCl. An organic layer was separated, washed with water, dried over anhydrous sodium sulfate, and concentrated. The resulting residue was purified by column chromatography (filler: Wakogel C-300, eluent: a mixed solvent of n-hexane and chloroform) to give yellow crystals of 3-acetyl-2-methyl-5-phenylthiophene in yield of 60%.

(4) Synthesis of diethylisopropylidene succinate

Sodium hydride in an amount of 2 moles was suspended in 1.0 liter of toluene and heated at 40° C. To this, a mixed solution of 1 mole of diethyl succinate and 1.2 moles of acetone was added dropwise in 3 hours with stirring. The reaction was carried out for further 3 hours. Then, the reaction solution was poured into 1 kg of ice. The water layer was separated, made acidic by pouring 700 ml of 5M HCl thereinto, and extracted with 1.0 liter of 1,2-dichloroethane. The resulting organic layer was dried over anhydrous sodium sulfate, and concentrated. To the resulting residue, 1.0 liter of ethanol and 30 ml of concentrated sulfuric acid were added.

The reaction was carried out under reflux for 4 hours. After the reaction, the solvent was removed from the reaction solution by distillation. The objected substance was extracted with dichloromethane and purified by distillation under reduced pressure to give diethylisopropylidene succinate in yield of 51%.

(5) Synthesis of 2-[(E)-1-(2-methyl-5-phenyl-3-thienyl)ethylidene]-3-isopropylidene succinic anhydride To a suspension of 700 ml of benzene and 52.8 g of sodium hydride, a mixed solution of 119 g of the 3-acetyl-2-methyl-5-phenylthiophene obtained in above (3) and 118 g of the diethylisopropylidene succinate obtained in above (4) was added dropwise in 2 hours with stirring. After further 7 hours' reaction with stirring, the reaction solution was poured into 2 kg of ice. The water layer was separated, made acidic by pouring 690 ml of 5M HCl thereinto, and extracted with 1.5 liters of ethyl acetate. The resulting organic layer was concentrated. To the residue, 1.85 liters of 5 w/v% ethanolic potassium hydroxide was added and the reaction was carried out under reflux for 15 hours. After the reaction, the reaction solution was made acidic with HCl. A precipitate produced was dissolved in chloroform. After removing the solvent from the obtained chloroform solution by distillation, acetyl chloride was added to the residue to carry out the ring closing reaction. After the reaction, excess acetyl chloride was removed by distillation. The residue was purified by column chromatography (filler: Wakogel C-300, eluent: a mixed solvent of n-hexane and ethyl acetate) to give pale yellow crystals of 2-[(E)-1-(2-methyl-5-phenyl-3-thienyl)ethylidene]-3-isopropylidene succinic anhydride of the formula:

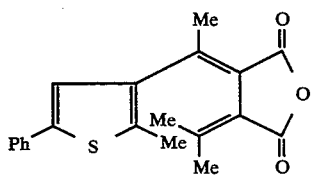

wherein Me is a methyl group, and Ph is a phenyl group, in yield of 15%.

REFERENCE EXAMPLE 2

Synthesis of 2-[(E)-1-(2,5-dimethyl-3-furyl)ethylidene]-3-isopropylidene succinic anhydride To a suspension of 700 ml of benzene with 52.8 g of sodium hydride, 118 g of a mixed solution 76 g of 3-acetyl-2,5-dimethylfuran (mfd. by Sldrich Chemical Co., Inc.) and 118 g of the diethylisopropylidene succinate obtained in Reference Example 1 (4) was added dropwise in 2 hours with stirring. After reacting for further 7 hours with stirring, the reaction solution was poured into 2 kg of ice. The water layer was separated, made acidic with 690 ml of 5M HCl, and extracted with 1.5 liters of ethyl acetate. The resulting organic layer was concentrated. To the residue, 1.85 liters of 5 w/v% ethanolic potassium hydroxide was added and reaction was carried out for 15 hours under relux. After the reaction, the reaction solution was made acidic with HCl. A precipitate produced was dissolved in chloroform. The solvent was removed from the resulting chloroform solution by distillation. To the residue, acetyl chloride was added and ring closing reaction was carried out. After the reaction, excess acetyl chloride was removed by distillation. The residue was purified by column chromatography (filler: Wakogel C-300, eluent: a mixed solvent of n-hexane and ethyl acetate) to give pale yellow crystals of 2-[(E)-1-(2,5-dimethyl-3-furyl)ethylidene]-3-isopropylidene succinic anhydride of the formula:

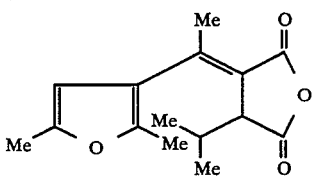

wherein Me is a methyl group, in yield of 15%.

REFERENCE EXAMPLE 3

Synthesis of 2-[(E)-1-(2,5-dimethyl-3-furyl)isobutylidene]-3-isopropylidene succinic anhydride (1) Synthesis of 3-isobutylyl-2,5-dimethyl-furan To a solution obtained by dissolving 1.1 moles of aluminum chloride in 200 ml of carbon tetrachloride and cooled at 0° C., a carbon tetrachloride solution containing 1 mole of 2,5-dimethylfuran and 1 mole of isobutylylfluorite was added dropwise with stirring in 2.0 hours. After reacting for further 2 hours with stirring, the reaction solution was poured into 1.5 kg of ice containing 400 ml of 6M HCl. An organic layer was separated, washed with water, dried over anhydrous sodium sulfate, and concentrated. The resulting residue was purified by distillation under reduced pressure to yield a yellow oil of 3-isobutylyl-2,5-dimethylfuran in yield of 40%.

(2) To a suspension of 500 ml of toluene containing 50 g of sodium hydride, a mixed solution of 83 g of 3-isobutylyl-2,5-dimethylfuran and 107 g of diethylisopropylidene succinate obtained in Reference Example 1 (4) was added dropwise with stirring in 2 hours. After reacting for further 3 hours with stirring, the reaction solution was poured in 2 kg of ice. A water layer was separated and made acidic by pouring 375 ml of 5M HCl thereinto. Then, the reaction solution was extracted with 1.5 liters of ethyl acetate. The resulting organic layer was concentrated. To the residue, 1.85 liters of 5 w/v% ethanolic potassium hydroxide was added and reacted for 15 hours under reflux. After the reaction, the reaction solution was made acidic with HCl and a produced precipitated was dissolved in chloroform. After removing the solvent from the resulting chloroform solution by distillation, acetyl chloride was added to the residue to carry out a ring closing reaction. After the reaction, excess acetyl chloride was removed by distillation. The residue was purified by column chromatography (filler: Wakogel C-300, eluent: a mixed solvent of n-hexane and ethyl acetate) to give pale yellow crystals of 2-[(E)-1-(2,5-dimethyl-3-furyl)isobutylidene]-3-isopropylidene succinic anhydride of the formula:

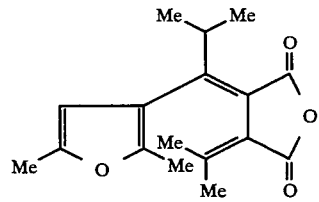

wherein Me is methyl, in yield of 19%.

REFERENCE EXAMPLE 4

Synthesis of 2-[(E)-1-(2,5-dimethyl-3-thienyl)isobutylidene]-3-isopropylidene succinic anhydride (1) Synthesis of 3-isobutylyl-2,5-dimethylthiophene To a carbon tetrachloride solution containing 1.1 moles of aluminum chloride cooled at 0° C., a carbon tetrachloride solution containing 1 mole of 2,5-dimethylthiophene and 1 mole of isobutylyl chloride was added dropwise in 2 hours. After reacting for further 10 hours with stirring, the reaction solution was poured into 1.5 kg of ice containing 400 ml of 6M HCl. An organic layer was separated, washed with water, dried over anhydrous sodium sulfate, and concentrated. The resulting residue was purified by distillation under reduced pressure to give a yellow oil of 3-isobutylyl-2,5-dimethylthiophene in yield of 60%.

(2) To a solution obtained by dissolving 61 g of diisopropylamine in 400 ml of tetrahydrofuran, 280 ml of n-butyllithium was added at low temperatures ($-10°\sim-40°$ C.), and 71 g of diethylisopropylidene succinate obtained in Reference Example 1 (4) and 55 g of 3-isobutylyl-2,5-dimethylthiophene were added dropwise in 30 minutes with stirring. After reacting for further 8 hours with stirring, the reaction solution was made acidic by pouring 1050 ml of 10% HCl thereinto, followed by extraction with 1.5 liters of ethyl acetate. The resulting organic layer was concentrated. To the residue, 1.85 liters of 5 w/v% ethanolic potassium hydroxide was added and the reaction was carried out for 15 hours under reflux. After the reaction, the reaction solution was made acidic with HCl and a precipitate produced was dissolved in chloroform. After removing the solvent from the resulting chloroform solution by distillation, acetyl chloride was added to the residue to carry out a ring closing reaction. After the reaction, excess acetyl chloride was removed by distillation. The residue was purified by column chromatography (filler: Wakogel C-300, eluent: a mixed solvent of n-hexane and ethyl acetate) to give pale yellow crystals of 2-[(E)-1-(2,5-dimethyl-3-thienyl)isobutylidene]-3-isopropylidene succinic anhydride of the formula:

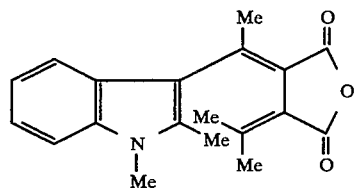

wherein Me is methyl, in yield of 1%.

REFERENCE EXAMPLE 5

Synthesis of 2-[(E)-1-(1,2-dimethyl-3-indolyl)ethylidene]-3-isopropylidene succinic anhydride (1) Synthesis of 3-acetyl-1,2-dimethylindole To a solution of 6 moles of N,N-dimethylacetamide and cooled at 0° C., 1.5 moles of phosphorus oxychloride was added dropwise in 30 minutes with stirring. After further adding 1 mole of 1,2-dimethylindole thereto, the reaction was carried out at 85°–90° C. for 2 hours. Then, the reaction solution was poured into 2 liters of ice water. The reaction solution was made alkaline, extracted with 0.5 liter of ethyl acetate, washed with water, dried over anhydrous sodium sulfate, and concentrated. The residue was recrystallized from ethyl acetate to give yellow crystals in yield of 80%.

(2) To a solution obtained by dissolving 76 g of diisopropylamine in 750 ml of tetrahydrofuran, 350 ml of n-butyllithium was added at low temperatures ($-10°\sim-40°$ C.), and 91 g of diethylisopropylidene succinate obtained in Reference Example 1 (4) and 70 g of 3-acetyl-1,2-dimethylindole were added dropwise with stirring in 30 minutes. After further reacting for 8 hours with stirring, the reaction solution was made acidic by pouring 1050 ml of 10% HCl thereinto, followed by extraction with 1.5 liters of ethyl acetate. The resulting organic layer was concentrated. The residue was added with 1.85 liters of 5 w/v% ethanolic potassium hydroxide and reacted for 15 hours under reflux. After the reaction, the reaction solution was made acidic with HCl and a precipitate produced was dissolved in chloroform. After removing the solvent from the chloroform solution by distillation, acetyl chloride was added to the residue to carry out a ring closing reaction. After the reaction, excess acetyl chloride was removed by distillation. The residue was purified by column chromatography (filler: Wakogel C-300, eluent: a mixed solvent of n-hexane and ethyl acetate) to give pale yellow crystals of 2-[(E)-1-(1,2-dimethyl-3-indolyl)ethylidene]-3-isopropylene succinic anhydride of the formula:

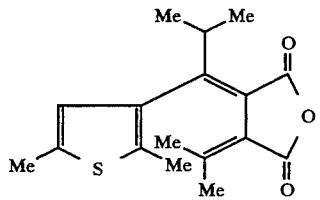

wherein Me is methyl, in yield of 6%.

REFERENCE EXAMPLE 6

Synthesis of 2-[(E)-1-(1,2-dimethyl-5-methoxy-3-indolyl)ethylidene]-3-isopropylidene succinic anhydride (1) Synthesis of 3-acetyl-5-methoxy-1,2-dimethylindole To an acetone solution containing 1 mole of p-quinone, an acetone solution containing 1 mole of acetylacetonemonomethylimine was added dropwise at room temperature in 1.0 hour. After reacting for further 1 hour with stirring, the reaction solution was filtered to obtain brown crystals. The crystals were dissolved in 1 liter of 1,4-diethylene glycol and 5 moles of 2N sodium hydroxide. To the resulting solution, 1.5 moles of dimethyl sulfate was added dropwise in 1 hour at room temperature. After reacting for further 2 hours with stirring, the reaction solution was poured into 1.5 liters of ice containing HCl. The resulting solution was extracted with 1 liter of ethyl acetate, washed with water, dried over anhydrous sodium sulfate, and concentrated. The resulting residue was purified by column chromatography (filler: Wakogel C-300, eluent: a mixed solvent of chloroform and methanol) to give yellow crystals of 3-acetyl-5-methoxy-1,2-dimethylindole in yield of 16%.

(2) To a solution obtained by dissolving 76 g of diisopropylamine in 750 ml of tetrahydrofuran, 350 ml of n-butyllithium was added at low temperatures ($-10°\sim-40°$ C.), and 91 g of diethylisopropylidene succinate obtained in Reference Example 1 (4) and 81 g of 3-acetyl-5-methoxy-1,2-dimethylindole were added dropwise thereto in 30 minutes with stirring. After reacting for further 8 hours with stirring, the reaction solution was made acidic by pouring 1050 ml of 10% HCl thereinto, followed by extraction with 1.5 liters of ethyl acetate. The resulting organic layer was concentrated. To the residue, 1.85 liters of 5 w/v% ethanolic potassium hydroxide was added to carry out the reaction for 15 hours under reflux. After the reaction, the reaction solution was made acidic with HCl. A precipitate produced was dissolved in chloroform. After removing the solvent from the resulting chloroform solution by distillation, acetyl chloride was added to the residue to carry out a ring closing reaction. The residue was purified by column chromatography (filler: Wakogel C-300, eluent: a mixed solvent of n-hexane and ethyl acetate) to give pale yellow crystals of 2-[(E)-1-(1,2-dimethyl-5-methoxy-3-indolyl)ethylidene]-3-isopropylidene succinic anhydride of the formula:

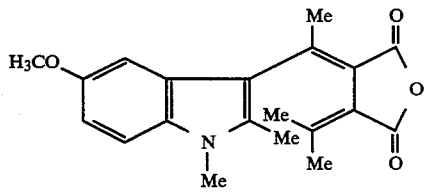

wherein Me is methyl, in yield of 5%.

EXAMPLE 1

Synthesis of N-(4-aminophenyl)-2-[(E)-1-(2,5-dimethyl-3-furyl)ethylidene]-3-isopropylidenesuccinimide To 20 ml of xylene, 1.04 g of (E)-2-[1-(2,5-dimethyl-3-furyl)ethylidene]-3-isopropylidene succinic anhydride obtained in Reference Example 2 and 0.216 g of p-phenylenediamine were added to carry out the reaction for 30 hours with stirring under reflux. After the reaction, the xylene was removed by distillation. The resulting residue was purified by column chromatography (filler: Wakogel C-300, eluent: a mixed solvent of n-hexane and ethyl acetate) to give pale red crystals of N-(4-aminophenyl)-2-[(E)-1-(2,5-dimethyl-3-furyl)ethylidene]-3-isopropylidenesuccinimide in yield of 12.0%.

m.p.: 209°–211° C.
MS: 350 (M+), 335 (M+ — 15)
Elementary analysis:

|  | C | H | N |
| --- | --- | --- | --- |
| Calcd. (%) | 71.99 | 6.33 | 7.99 |
| Found (%) | 71.55 | 6.24 | 7.90 |

IR (KBr) cm$^{-1}$: 3375 (NH$_2$), 2800–3000 (CH$_2$, CH$_3$), 1740, 1700 (NCO, CO), 1510 (phenyl), 760, 780 (furyl)

$^1$HNMR (CDCl$_3$) δ ppm: 1.35 (3H, s, CH$_3$), 2.01 (3H, s, CH$_3$), 2.17 (3H, s, CH$_3$), 2.28 (3H, s, CH$_3$), 2.40 (3H, s, CH$_3$), 5.88 (1H, s, H), 6.5–7.3 (4H, q, phenyl)

When the obtained N-(4-aminophenyl)-2-[(E)-1-(2,5-dimethyl-3-furyl)ethylidene]-3-isopropylidenesuccinimide was dissolved in chloroform and exposed to ultraviolet light of 310-380 nm [light source: ultra-high pressure mercury lamp (mfd. by Ushio Inc.), filter: UV-35 and UVD-35 (trade names, mfd. by Toshiba Glass Co., Ltd.)] for 1 minute, the color of the solution was changed to deep red (λ$_{max}$: 518 nm). In the next place, when the solution was exposed to visible light of 470 nm or more [light source: 250W Xe lamp (mfg. by Ushio Inc.), filter: IRA-25S and Y-47 (trade names, mfd. by Toshiba Glass Co., Ltd.)] for 1 minute, the solution showed the state before the exposure to ultraviolet light. The above mentioned procedures were repeated a number of times, and the results were the same at every repetition.

EXAMPLE 2

Synthesis of N-(4-aminophenyl)-2-[(E)-1-(2 -methyl-5-phenyl-3 -thienyl)ethylidene]-3 -isopropyl idenesuccinimide To 20 ml of xylene, 2.03 g of 2-[(E)-i-(2-methyl-5-phenyl-3-thienyl)ethylidene]-3-isopropylidene succinic anhydride obtained in Reference Example 1 and 0,324 g of p-phenylenediamine were added to carry out the reaction for 30 hours with stirring under reflux. After the reaction, the xylene was removed by distillation. The resulting residue was purified by column chromatography (filler: Wakogel C-300, eluent: a mixed solvent of n-hexane and ethyl acetate) to give pale red crystals of N-(4-aminophenyl)-2-[(E)-1-(2-methyl-5-phenyl-3-thienyl)ethylidene]-3-isopropylidenesuccinimide in yield of 6.0%.

m.p.: 193°–195° C.
MS: 428 (M+), 413 (M+ — 15)
Elementary analysis:

|  | C | H | N |
| --- | --- | --- | --- |
| Calc. (%) | 72.88 | 5.64 | 6.53 |
| Found (%) | 71.84 | 5.83 | 6.28 |

IR (KBr): 3375 (NH$_2$), 2800–3000 (CH$_2$, CH$_3$), 1740, 1690 (NCO, CO), 152.0 (phenyl), 750, 690 (thienyl)

$^1$HNMR (CDCl$_3$): 1.35 (3H, s, CH$_3$), 2.29 (6H, s, CH$_3$×2), 2.68 (3H, s, CH$_3$), 7.10 (1H, s, H), 7.19–7.56 (9H, m, phenyl)

When the obtained N-(4-aminophenyl)-2-[(E)-1-( 2-methyl-5-phenyl-3-thienyl)ethylidene]-3-isopropylidenesuccinimide was dissolved in chloroform and exposed to ultraviolet light of 310–380 nm [light source: ultra-high pressure mercury lamp (mfd. by Ushio Inc.), filter: UV-35 and UVD-35 (mfd. by Toshiba Glass Co., Ltd. )] for 1 minute, the solution was changed to deep reddish violet (λ$_{max}$: 554 nm). In the next place, when the solution was exposed to visible light of 500 nm or more [light source: 250W Xe lamp (mfd. by Ushio Inc.), filter: IRA-25S and O-54 (trade names, mfd. by Toshiba Glass Co., Ltd. )] for 1 minute, the solution showed the state before the exposure to ultraviolet light. The above-mentioned procedures repeated a number of times, and the results were the same at every repetition.

EXAMPLE 3

Synthesis of N-(5-amino-1-naphthyl)-2-[(E)-1-(2-methyl-5-phenyl-3-thienyl) ethylidene]-3-isopropylidenesuccinimide The process of Example 2 was repeated except for using 1,5-diaminonaphthalene in place of p-phenylenediamine to give N-(5-amino-1-naphthyl)-2-[(E)-1-(2-methyl-5-phenyl-3 -thienyl)ethylidene] -3 -isopropylidenesuccinimide in yield of 10.0%.

m.p.: 155°–158° C.
MS: 478 (M+)
Elementary analysis:

|        | C     | H    | N    |
|--------|-------|------|------|
| Calcd. (%) | 75.28 | 5.47 | 5.85 |
| Found (%)  | 74.81 | 5.72 | 5.63 |

UV ($\lambda_{max}$ in chloroform, after irradiation of ultraviolet light): 556 nm, IR (KBr): 3375 ($NH_2$), 2800–3000 ($CH_2$, $CH_3$), 1750, 1700 (NCO), 1520 (phenyl), 750, 690 (thienyl)

$^1$HNMR ($CDCl_3$): 1.41 (3H, s, $CH_3$), 2.81 (6H, s, $CH_3 \times 2$), 2.71 (3H, s, $CH_3$), 7.14 (1H, s, H), 7.36–7.58 (11H, m, aromatic)

EXAMPLE 4

Synthesis of N-[4-(4-aminobenzyl) phenyl]-2-[(E)-1-(2-methyl-5-phenyl-3-thienyl) ethylidene]-3-isopropylidenesuccinimide The process of Example 2 was repeated by using 4,4'-methylenebis (aniline) in place of p-phenylenediamine to give N-[4-(4-aminobenzyl) phenyl]-2-[(E)-1-(2-methyl-5-phenyl-3-thienyl) ethylidene]-3-isopropylidenesuccinimide in yield of 11.2%.

m.p.: 82°–94° C.
MS: 518 (M+)
Elementary analysis:

|        | C     | H    | N    |
|--------|-------|------|------|
| Calcd. (%) | 76.42 | 5.30 | 5.40 |
| Found (%)  | 75.68 | 5.52 | 5.10 |

IR (KBr): 3375 ($NH_2$), 2800–3000 ($CH_2$, $CH_3$), 1740, 1760 (NCO), 1510 (phenyl), 760, 690 (thienyl)

$^1$HNMR ($CDCl_3$): 1.24 (3H, s, $CH_3$), 2.29 (6H, s, $CH_3 \times 2$), 2.68 (3H, s, $CH_3$), 3.95 (2H, s, $CH_2$), 7.10 (1H, s, H), 7.36–7.56 (13H, m, aromatic)

EXAMPLE 5

Synthesis of N-(4-hydroxyphenyl)-2-[(E)-1-(2,5-dimethyl-3-furyl)ethylidene]-3-isopropylidenesuccinimide To 30 ml of toluene, 1.3 g of 2-[(E)-1-(2,5-dimethyl-3-furyl)ethylidene]-3-isopropylidene succinic anhydride obtained in Reference Example 2 and 0.55 g of p-aminophenol were added to carry out the reaction for 30 hours with stirring under reflux. After the reaction, the toluene was removed by distillation. The resulting residue was purified by column chromatography (filler: Wakogel C-300, eluent: a mixed solvent of n-hexane and ethyl acetate) to give red crystals of N-(4-hydroxyphenyl)-2-[(E)-1-(2,5-dimethyl-3-furyl)ethylidene]-3-isopropylidenesuccinimide in yield of 36.0%.

m.p.: 206°–208° C.
MS: 351 (M+)
Elementary analysis:

|        | C     | H    | N    |
|--------|-------|------|------|
| Calcd. (%) | 71.77 | 6.02 | 3.98 |
| Found (%)  | 71.50 | 6.26 | 3.74 |

UV ($\lambda_{max}$ in toluene): 320 nm (after irradiation of ultraviolet light: 503 nm)

IR (KBr): 3450 ($NH_2$), 2800–3000 ($CH_2$, $CH_3$), 1740, 1690 (NCO), 1520, 1600 (phenyl), 1390, 1440 ($CH_3$)

$^1$HNMR ($CDCl_3$): 1.40 (3H, s, $CH_3$), 2.10 (3H, s, $CH_3$), 2.30 (3H, s, $CH_3$), 2.40 (3H, s, $CH_3$), 2.60 (3H, s, $CH_3$), 5.90 (1H, s, H), 6.4–7.3 (4H, q, phenyl)

EXAMPLE 6

Synthesis of N-(2-hydroxyethyl)-2-[(E)-1-(2,5-dimethyl-3-furyl)ethylidene]-3-isopropylidenesuccinimide The process of Example 5 was repeated except for using 1-aminoethanol in place of p-aminophenol to give an orange oil of N-(2-hydroxyethyl)-2-[(E)-1-(2,5-dimethyl-3-furyl)ethylidene]-3-iospropylidenesuccinimide in yield of 25.4%.

Elementary analysis:

|        | C     | H    | N    |
|--------|-------|------|------|
| Calcd. (%) | 67.31 | 6.98 | 4.62 |
| Found (%)  | 67.20 | 7.21 | 4.49 |

UV ($\lambda_{max}$ in toluene): 324 nm (after irradiation of ultraviolet light: 500 nm)

IR (nujol): 3500 (OH), 2800–3000 ($CH_2$, $CH_3$), 1740, 1690 (NCO), 1040 (OH)

$^1$HNMR ($CDCl_3$): 1.33 (3H, s, $CH_3$), 1.98 (3H, s, $CH_3$), 2.23 (3H, s, $CH_3$), 2.30 (3H, s, $CH_3$), 2.42 (3H, s, $CH_3$), 2.83 (1H, s, OH), 3.97–3.67 (4H, m, $CH_2 \times 2$), 5.76 (1H, s, H)

EXAMPLE 7

Synthesis of N-(6-hydroxyhexyl)-2-[(E)-1-(2,5-dimethyl-3-furyl)ethylidene]-3-isopropylidenesuccinimide The process of Example 5 was repeated except for using 1-aminohexanol in place of p-aminophenol to give an orange oil of N-(6-hydroxyhexyl)-2-[(E)-1-(2,5-dimethyl-3-furyl)ethylidene]-3-isopropylidenesuccinimide in yield of 10.2%.

Elementary analysis:

|        | C     | N    | H    |
|--------|-------|------|------|
| Calcd. (%) | 70.17 | 8.13 | 3.90 |
| Found (%)  | 69.29 | 8.02 | 3.67 |

UV ($\lambda_{max}$ in toluene): 316 nm (after irradiation of ultraviolet light: 496 nm)

EXAMPLE 8

Synthesis of N-(4-hydroxyphenyl)-2-[(E)-1-(2-methyl-5-phenyl-3-thienyl)ethylidene]-3-isopropylidenesuccinimide To 30 ml of toluene, 3.38 g of 2-[(E)-1-(2-methyl-5-phenyl-3-thienyl)ethylidene]-3-isopropylidene succinic anhydride obtained in Reference Example 1 and 1.1 g of p-aminophenol were added to carry out the reaction for 30 hours with stirring under reflux. After the reaction, the toluene was removed by distillation. The resulting residue was purified by column chromatography (filler: Wakogel C-300, eluent: a mixed solvent of n-hexane and ethyl acetate) to give N-(4-hydroxyphenyl)-2-[(E)-1-(2-methyl-5-phenyl-3-thienyl) ethylidene]-3-isopropylidenesuccinimide in yield of 36%.

m.p.: 213°–215° C.
MS: 429 (M+)
Elementary analysis:

|        | C     | H    | N    |
|--------|-------|------|------|
| Calcd. (%) | 72.71 | 5.39 | 3.26 |
| Found (%)  | 72.56 | 5.31 | 3.18 |

IR (KBr): 3400 (OH), 2800–3000 (CH₂, CH₃), 1740, 1680 (NCO), 830, 750 (thienyl)

EXAMPLE 9

Synthesis of N-(2-hydroxyethyl)-2-[(E)-1-(2-methyl-5-phenyl-3-thienyl)ethylidene]-3-isopropylidenesuccinimide The process of Example 8 was repeated except for using 1-aminoethanol in place of p-aminophenol to give reddish violet crystals of N-(2-hydroxyethyl)-2-[(E)-1-(2-methyl-5-phenyl-3-thienyl)ethylidene]-3-isopropylidenesuccinimide in yield of 21.3%.

Elementary analysis:

|  | C | H | N |
|---|---|---|---|
| Calcd. (%) | 69.26 | 6.07 | 3.67 |
| Found (%) | 68.14 | 6.08 | 3.15 |

UV ($\lambda_{max}$ in toluene, after irradiation of ultraviolet light): 542 nm.

EXAMPLE 10

Synthesis of N-(4-aminophenyl)-2-[(E)-1-(2,5-dimethyl-3-furyl)isobutylidene]-3-isopropylidenesuccinimide To 20 ml of xylene, 2.88 g of (E)-2-[1-(2,5-dimethyl-3-furyl)isobutylidene]-3-isopropylidene succinic anhydride obtained in Reference Example 3 and 1.14 g of p-phenylenediamine were added to carry out the reaction for 30 hours with stirring under reflux. After the reaction, the xylene was removed by distillation. The resulting residue was purified by column chromatography (filler: Wakogel C-300, eluent: a mixed solvent of n-hexane and ethyl acetate) to give yellow crystals of N-(4-aminophenyl)-2-[(E)-1-(2,5-dimethyl-3-furyl)isobutylidene]-3-isopropylidenesuccinimide in yield of 28.0%.

m.p.: 150°–152° C.
MS: 378 (M+), 363 (M+−15)
Elementary analysis:

|  | C | H | N |
|---|---|---|---|
| Calcd. (%) | 72.99 | 6.92 | 7.40 |
| Found (%) | 73.12 | 6.98 | 7.42 |

UV ($\lambda_{max}$ in chloroform): 520 nm

EXAMPLE 11

Synthesis of N-(4-hydroxyphenyl)-2-[(E)-1-(2,5-dimethyl-3-thienyl)isobutylidene]-3-isopropylidenesuccinimide To 20 ml of xylene, 3.05 g of (E)-2-[1-(2,5-dimethyl-3-thienyl)isobutylidene]-3-isopropylidene succinic anhydride obtained in Reference Example 4 and 1.1 g of p-aminophenol were added to carry out the reaction for 30 hours with stirring under reflux. After the reaction, the xylene was removed by distillation. The resulting residue was purified by column chromatography (filler: Wakogel C-300, eluent: a mixed solvent of n-hexane and ethyl acetate) to give yellow crystals of N-(4-hydroxyphenyl)-2-[(E)-1-(2,5-dimethyl-3-thienyl)isobutylidene]-3-isopropylidenesuccinimide in yield of 28.0%.

m.p.: 136°–138° C.
MS: 395 (M+), 380 (M+−15)
Elementary analysis:

|  | C | H | N |
|---|---|---|---|
| Calcd. (%) | 69.93 | 6.38 | 3.54 |
| Found (%) | 69.98 | 6.45 | 3.50 |

UV ($\lambda_{max}$ in chloroform): 550 nm

EXAMPLE 12

Synthesis of N-(4-stearoylaminophenyl)-2-[(E)-1-(2,5-dimethyl-3-furyl) isobutylidene]-3-isopropylidenesuccinimide To 20 ml of xylene, 2.88 g of (E)-2-[1-(2,5-dimethyl-3-furyl)isobutylidene]-3-isopropylidene succinic anhydride obtained in Reference Example 3 and 1.44 g of p-phenylenediamine were added to carry out the reaction for 30 hours with stirring under reflux. After the reaction, 20 ml of pyridine and 3 g of stearoyl chloride were added to the reaction mixture to carry out the reaction for 1 hour. Then, the xylene was removed by distillation. The resulting residue was purified by column chromatography (filler: Wakogel C-300, eluent: a mixed solvent of n-hexane and ethyl acetate) to give yellow crystals of N-(4-stearoylamidophenyl)-2-[(E)-1-(2,5-dimethyl-3-furyl) isobotylidene]-3-isopropylidenesuccinimide in yield of 18.0%.

m.p.: 68°–70° C.
MS: 645 (M+), 620 (M+−15)
Elementary analysis:

|  | C | H | N |
|---|---|---|---|
| Calcd. (%) | 76.35 | 9.38 | 4.34 |
| Found (%) | 76.21 | 9.32 | 4.30 |

UV ($\lambda_{max}$ in chloroform): 522 nm

EXAMPLE 13

Synthesis of N-(4-carboxyphenyl)-2-[(E)-1-(2,5-dimethyl-3-furyl)isobutylidene]-3-iosropylidenesuccinimide To 20 ml of xylene, 2.88 g of (E)-2-[1-(2,5-dimethyl-3-furyl) isobutylidene]-3-isopropylidene succinic anhydride obtained in Reference Example 3 and 2.74 g of 4-aminobenzoic acid were added to carry out the reaction for 30 hours with stirring under reflux. After the reaction, the xylene was removed by distillation. The resulting residue was purified by column chromatography (filler: Wakogel C-300, eluent: a mixed solvent of n-hexane and ethyl acetate) to give yellow crystals of N-(4-carboxyphenyl)-2-[(E)-1-(2,5-dimethyl-3-furyl)isobutylidene]-3-isopropylidenesuccinimide in yield of 9.0%.

m.p.: 195°–197° C.
MS: 408 (M+), 393 (M+−15)
Elementary analysis:

|  | C | H | N |
|---|---|---|---|
| Calcd. (%) | 70.64 | 6.42 | 3.43 |
| Found (%) | 70.58 | 6.40 | 3.41 |

UV ($\lambda_{max}$ in chloroform): 520 nm

EXAMPLE 14

Synthesis of N-(4-carboxymethyl)-2-[(E)-1-(2,5-dimethyl-3-furyl)isobutylidene]-3-isopropylidenesuccinimide To 20 ml of xylene, 2.88 g of (E)-2-[1-(2,5-dimethyl-3-furyl)isobutylidene]-3-isopropylidene succinic anhydride obtained in Reference Example 3 and 3.0 g of p-aminophenylacetic acid were added to carry out the reaction for 30 hours with stirring under reflux. After the reaction, the xylene was removed by distillation. The resulting residue was purified by column chromatography (filler: Wakogel C-300, eluent: a mixed solvent of n-hexane and ethyl acetate) to give yellow crystals of N-(4-carboxymethyl)-2-[(E)-1-(2,5-dimethyl-3-furyl)isobutylidene-3-isopropylidenesuccinimide in yield of 25.0%.

m.p.: 154°–156° C.
MS: 421 (M+), 406 (M+−15)
Elementary analysis:

|  | C | H | N |
| --- | --- | --- | --- |
| Calcd. (%) | 71.30 | 6.46 | 3.32 |
| Found (%) | 71.28 | 6.45 | 3.33 |

UV ($\lambda_{max}$ in chloroform): 520 nm

EXAMPLE 15

Synthesis of N-(2-aminofluorene)-2-[(E)-1-(2,5-dimethyl-3-furyl)isobutylidene]-3-isopropylidenesuccinimide To 20 ml of xylene, 2.88 g of (E)-2-[1-(2,5-dimethyl-3-furyl)isobutylidene]-3-isopropylidene succinic anhydride obtained in Reference Example 3 and 4.0 g of 2,7-diaminofluorene were added to carry out the reaction for 30 hours with stirring under reflux. After the reaction, the xylene was removed by distillation. The resulting residue was purified by column chromatography (filler: Wakogel C-300, eluent: a mixed solvent of n-hexane and ethyl acetate) to give yellow crystals of N-(2-aminofluorene)-2-[(E)-1-(2,5-dimethyl-3-furyl)-isobutylidene]-3-isopropylidene succinimide in yield of 25.0%.

m.p.: 190°–192° C.
467 (M+), 452 (M+-15)
Elementary analysis:

|  | C | H | N |
| --- | --- | --- | --- |
| Calcd. (%) | 77.23 | 6.48 | 6.00 |
| Found (%) | 77.12 | 6.40 | 5.98 |

UV ($\lambda_{max}$ in chloroform): 522 nm

EXAMPLE 16

Synthesis of N-(4-hydroxyphenyl)-2-[(E)-1-(1,2-dimethyl-3-indolyl) ethylidene]-3-isopropylidenesuccinimide To 20 ml of xylene, 3.09 g of (E)-2-[1-(1,2-dimethyl-3-indolyl) ethylidene]-3-isopropylidenesuccinic anhydride obtained in Reference Example 5 and 2.2 g of p-aminophenol were added to carry out the reaction for 30 hours with stirring under reflux. After the reaction, the xylene was removed by distillation. The resulting residue was purified by column chromatography (filler: Wakogel C-300, eluent: a mixed solvent of n-hexane and ethyl acetate) to give yellow crystals of N-(4-hydroxyphenyl)-2-[(E)-1-(1,2-dimethyl-3-indolyl) ethylidene]-3-isopropylidenesuccinimide in yield of 25.0%.
m.p.: 231°–233° C.
MS: 400 (M+), 385 (M+−15)
Elementary analysis:

|  | C | H | N |
| --- | --- | --- | --- |
| Calcd. (%) | 74.98 | 6.04 | 6.99 |
| Found (%) | 74.67 | 6.00 | 6.92 |

UV ($\lambda_{max}$ in chloroform): 585 nm

EXAMPLE 17

Synthesis of N-(4-aminophenyl)-2-[(E)-1-(1,2-dimethyl-5-methoxy-3-indolyl)ethylidene]-3-isopropylidenesuccinimide To 20 ml of xylene, 3.40 g of (E)-2-[1-(1,2-dimethyl-5-methoxy-3-indolyl)ethylidene]-3-isopropylidene succinic anhydride obtained in Reference Example 6 and 2.2 g of p-phenylene diamine were added to carry out the reaction for 30 hours with stirring under reflux. After the reaction, the xylene was removed by distillation. The resulting residue was purified by column chromatography (filler: Wakogel C-300, eluent: a mixed solvent of n-hexane and ethyl acetate) to give yellow crystals of N-(4-aminophenyl)-2-[(E)-1-(1,2-dimethyl-5-methoxy-3-indolyl) ethylidene]-3-isopropylidenesuccinimide in yield of 20.0%.

m.p.: 195°–197° C.
MS: 429 (M+), 414 (M+−15)
Elementary analysis:

|  | C | H | N |
| --- | --- | --- | --- |
| Calcd. (%) | 72.71 | 6.33 | 9.78 |
| Found (%) | 72.65 | 6.25 | 9.72 |

UV ($\lambda_{max}$ in chloroform): 620 nm

EXAMPLE 18

Synthesis of N-(4-hydroxyphenyl)-2-[(E)-1-(2,5-dimethyl-3-furyl)isobutylidene]-3-isopropylidenesuccinimide To 30 ml of toluene, 1.3 g of 2-[(E)-i-(2,5-dimethyl-3-furyl)isobutylidene]-3-isopropylidene succinic anhydride obtained in Reference Example 3 and 0.55 g of p-aminophenol were added to carry out the reaction for 30 hours with stirring under reflux. After the reaction, the toluene was removed by distillation. The resulting residue was purified by column chromatography (filler: Wakogel C-300, eluent: a mixed solvent of n-hexane and ethyl acetate) to give yellow crystals of N-(4-hydroxyphenyl)-2-[(E)-1-(2,5-dimethyl-3-furyl)isobutylidene]-3-isopropylidenesuccinimide in yield of 36.0%.

m.p.: 170°–172° C.
MS: 379 (M+)
Elementary analysis:

|  | C | H | N |
| --- | --- | --- | --- |
| Calcd. (%) | 72.80 | 6.64 | 3.69 |
| Found (%) | 72.71 | 6.58 | 3.68 |

UV ($\lambda_{max}$ in chloroform): 330 nm (after irradiation of ultraviolet light: 520 nm)

IR (KBr) cm$^{-1}$: 2800–3000 ($CH_2$, $CH_3$), 1740, 1690 (NCO), 1520, 1600 (phenyl), 1390, 1440 ($CH_3$)

$^1$HNMR ($CDCl_3$) $\delta_{ppm}$: 0.87 (3H, bd, $CH_3$), 1.30 (3H, bd, $CH_3$), 1.40 (3H, s, $CH_3$), 1.90 (3H, s, $CH_3$), 2.26 (3H, s, $CH_3$), 2.28 (3H, s, $CH_3$), 4.50 (H, m, H), 5.90 (1H, s, H), 6.4–7.3 (4H, q, phenyl)

EXAMPLE 19

Synthesis of N-(4-acryloyloxyphenyl)-2-[(E)-1-(2,5-dimethyl-3-furyl)ethylidene]-3-isopropylidenesuccinimide To a solution obtained by dissolving 211 mg of N-(4-hydroxyphenyl)-2-[(E)-1-(2,5-dimethyl-3-furyl)ethylidene]-3-isopropylidenesuccinimide obtained in Example 5 in 5 ml of dichloromethane, 72 mg of triethylamine was added, followed by dropwise addition of 66 mg of acryloyl chloride in 10 minutes. The reaction was carried out at room temperature for 30 minutes with stirring. After the reaction, the reaction solution was well washed with water, dried over anhydrous magnesium sulfate, and subjected to removal of the solvent by distillation. The resulting residue was purified by column chromatography (filler: Wakogel C-300, eluent: a mixed solvent of n-hexane and ethyl acetate) to give pale red crystals of N-(4-acryloyloxyphenyl)-2-[(E)-1-(2,5-dimethyl-3-furyl)ethylidene]-3-isopropylidenesuccinimide in yield of 44.0%.

m.p.: 157°–158° C.
MS: 405 (M+)
Elementary analysis:

|  | C | H | N |
| --- | --- | --- | --- |
| Calcd. (%) | 71.10 | 5.72 | 3.47 |
| Found (%) | 70.94 | 5.48 | 3.53 |

UV ($\lambda_{max}$ in chloroform): 332 nm
IR (KBr) cm$^{-1}$: 2800–3000 ($CH_2$, $CH_3$), 1740, 1700 (NCO, COO), 1420, 1600 (phenyl), 1380 ($CH_3$)
$^1$HNMR ($CDCl_3$) δ ppm: 1.38 (3H, s, $CH_3$), 2.05 (3H, s, $CH_3$), 2.25 (3H, s, $CH_3$), 2.33 (3H, s, $CH_3$), 2.60 (3H, s, $CH_3$), 5.90 (1H, s, H), 6.0–6.5 (3H, m, allyl), 7.2–7.45 (4H, q, phenyl)

EXAMPLE 20

Synthesis of N-(4-methacryloyloxyphenyl)-2-[(E)-1-(2-methyl-5-phenyl-3-thienyl)ethylidene]-3-isopropylidenesuccinimide To a solution obtained by dissolving 430 mg of N-(4-hydroxyphenyl)-2-[(E)-1-(2-methyl-5-phenyl-3-thienyl)ethylidene]-3-isopropylidenesuccinimide obtained in Example 8 in 10 ml of dichloromethane, 202 mg of triethylamine was added, followed by dropwise addition of 209 mg of methacryloyl chloride in 10 minutes. The reaction was carried out at room temperature for further 1 hour. After the reaction, the reaction solution was washed with water, dried over anhydrous magnesium sulfate, and subjected to removal of the solvent by distillation. The resulting residue was purified by column chromatography (filler: Wakogel C-300, eluent: a mixed solution of n-hexane and ethyl acetate) to give organce crystals of N-(4-methacryloyloxyphenyl)-2-[(E)-1-(2-methyl-5-phenyl-3-thienyl)ethylidene]-3-isopropylidenesuccinimide in yield of 44.0%.

m.p.: 152°–153° C.
MS: 498 (M+)
Elementary analysis:

|  | C | H | N |
| --- | --- | --- | --- |
| Calcd. (%) | 72.41 | 5.46 | 2.81 |
| Found (%) | 72.17 | 5.47 | 2.57 |

IR (KBr) cm$^{-1}$: 2800–3000 ($CH_2$, $CH_3$), 1740, 1720, 1700 (NCO, COO), 1500 (phenyl), 1370, 1200, 1160 ($CH_3$), 770, 700 (thienyl)
$^1$HNMR ($CDCl_3$) δ ppm: 1.35 (3H, s, $CH_3$), 2.08 (3H, s, $CH_3$), 2.31 (6H, s, $CH_3 \times 2$), 2.70 (3H, s, $CH_3$), 5.77, 6.37 (2H, d, $CH_2$), 7.11 (1H, s, H), 7.23–7.56 (9H, m, phenyl)

EXAMPLE 21

Synthesis of N-(4-methacryloylaminophenyl)-2-[(E)-1-(2,5-dimethyl-3-furyl)ethylidene]-3-isopropylidenesuccinimide To a solution obtained by dissolving 105 mg of N-(4-aminophenyl)-2-[(E)-1-(2,5-dimethyl-3-furyl)ethylidene]-3-isopropylidenesuccinimide obtained in Example 1 in 2 ml of chloroform, 5 ml of pyridine was added, followed by dropwise addition of 0.84 ml of methacryloyl chloride in 10 minutes. The reaction was carried out at room temperature for additional 4 hours with stirring. After the reaction, the reaction solution was well washed with water, dried over anhydrous magnesium sulfate, and subjected to the removal of the solvent by distillation. The resulting residue was purified by column chromatography (filler: Wakogel C-300, eluent: a mixed solvent of n-hexane and ethyl acetate) to give yellow crystals of N-(4-methacryloylaminophenyl)-2-[(E)-1-(2,5-dimethyl-3-furyl)ethyliden]-3-isopropylidenesuccinimide in yield of 40.0%.

m.p.: 102°–104° C.
MS: 418 (M+)
Elementary analysis:

|  | C | H | N |
| --- | --- | --- | --- |
| Calcd. (%) | 71.75 | 6.29 | 6.69 |
| Found (%) | 71.35 | 6.82 | 6.72 |

IR (KBr) cm$^{-1}$: 2800–3000 ($CH_2$, $CH_3$), 1740, 1700 (NCO), 1510, 1600 (phenyl), 1370 ($CH_3$), 830, 750 (furyl)
$^1$HNMR ($CDCl_3$): δ ppm: 1.37 (3H, s, $CH_3$), 2.05 (3H, s, $CH_3$), 2.07 (3H, s, $CH_3$), 2.25 (3H, s, $CH_3$), 2.37 (3H, s, $CH_3$), 2.60 (3H, s, $CH_3$), 5.48, 5.80 (2H, d, $CH_2$), 5.94 (1H, s, H), 7.34–7.70 (4H, m, phenyl)

EXAMPLE 22

Synthesis of N-(4-acryloyloxyphenyl)-2-[(E)-1-( 2,5-dimethyl-3-furyl)isobutylidene]-3-isopropylidenesuccinimide To a solution obtained by dissolving 1.13 g of n-(4-hydroxyphenyl)-2-[(E)-1-(2,5-dimethyl-3-furyl)isobutylidene]-3-isopropylidenesuccinimide obtained in Example 18 in 30 ml of dichloromethane, 0.62 ml of triethylamine, followed by dropwise addition of 0.36 ml of acryloyl chloride in 10 minutes. The reaction was carried out at room temperature for additional 30 minutes with stirring. After the reaction, the reaction solution was well washed with water, dried over anhydrous magnesium sulfate, and subjected to removal of the solvent by distillation. The resulting residue was purified by column chromatography (filler: Wakogel C-300, eluent: a mixed solvent of n-hexane and ethyl acetate) to give yellow crystals of N-(4-acryloyloxyphenyl)-2-[(E)-1-(2,5-dimethyl-3-furyl) isobutylidene]-3-isopropylidenesuccinimide in yield of 60%.

m.p.: 50°–52° C.
MS: 433 (M+)
Elementary analysis:

|           | C     | H    | N    |
|-----------|-------|------|------|
| Calcd. (%) | 72.03 | 6.27 | 3.23 |
| Found (%)  | 71.76 | 6.21 | 3.15 |

UV ($\lambda_{max}$ in chloroform): 332 nm
IR (KBr) cm$^{-1}$: 2800–3000 (CH$_2$, CH$_3$), 1740, 1720, 1700 (NCO, COO), 1420, 1600 (phenyl), 1380 (CH$_3$)

EXAMPLE 23

Synthesis of N-(4-acryloyloxyphenyl)-2-[(E)-(1,2-dimethyl-3-indolyl)ethylidene]-3-isopropylidenesuccinimide To a solution obtained by dissolving 1.2 g of N-(4-hydroxyphenyl)-2-[(E)-1-(1,2-dimethyl-3-indolyl)ethylidene]-3-isopropylidenesuccinimide obtained in Example 16 in 25 ml of dichloromethane, followed by dropwise addition of 0.36 ml of acryloyl chloride in 10 minutes. The reaction was carried out at room temperature for additional 30 minutes with stirring. After the reaction, the reaction solution was well washed with water, dried over anhydrous magnesium sulfate, followed by removal of the solvent by distillation. The resulting residue was purified by column chromatography (filler: Wakogel C-300, eluent: a mixed solvent of n-hexane and ethyl acetate) to give yellow crystals of N-(4-acryloyloxyphenyl)-2-[(E)-1-(1,2-dimethyl-3-indolyl)ethylidene]-3-isopropylidenesuccinimide in yield of 88.5%.

m.p.: 172°–174° C.
MS: 455 (M+)
Elementary analysis:

|           | C     | H    | N    |
|-----------|-------|------|------|
| Calcd. (%) | 73.82 | 5.97 | 6.14 |
| Found (%)  | 73.76 | 6.03 | 6.10 |

UV ($\lambda_{max}$ in chloroform): 373 nm
IR (KBr) cm$^{-1}$: 2800–3300 (CH$_2$, CH$_3$), 1740, 1720, 1700 (NCO, COO), 1420, 1600 (phenyl), 1380 (CH$_3$)

EXAMPLE 24

Synthesis of polymer containing fulgimide derivative

To 6 ml of dimethylformamide, 0.1 g of N-(4-methacryloyloxyphenyl)-2-[(E)-1-(2-methyl-5-phenyl-3-thienyl)ethylidene]-3-isopropylidenesuccinimide obtained in Example 20 and 1.0 g of methyl methacrylate were added and subjected to stirring for 30 minutes, while bubbling nitrogen gas thereinto with heating by an outer bath temperature of 60° C. After adding 6.0 mg of azobisisobutyronitrile to the resulting solution, the reaction was carried out at 60° C. for further 8 hours with stirring. After the reaction, the reaction solution was poured into methanol containing a small amount of hydroquinone. Then, a precipitate produced was filtered and dissolved in acetone, followed by pouring into the methanol to reprecipitate, repeating these procedures three times. The finally obtained precipitate was dried in vacuum to give 230 mg of copolymer of N-(4-methacryloyloxyphenyl)-2-[(E)-1-(2-methyl-5-phenyl-3-thienyl) ethylidene]-3-isopropylidenesuccinimide [A] and methyl methacrylate [B] in yield of 21%.

The results of elementary analysis values of the copolymer revealed that the copolymerization ratio of [A] to [B] was about 1:10.6 (weight ratio).

REFERENCE EXAMPLE 7

Synthesis of N-(4-isobutylyloxyphenyl)-2-[(E)-1-(2-methyl-5-phenyl-3-thienyl)ethyliden]-3-isopropylidenesuccinimide To a solution obtained by dissolving 86 mg of N-(4-hydroxyphenyl)-2-[(E)-1-(2-methyl-5-phenyl-3thienyl)ethylidene]-3-isopropylidenesuccinimide obtained in Example 8 in 2 ml of dry dichloromethane, 0.1 ml of pyridine was added, followed by dropwise addition of a solution obtained by dissolving 43 mg of isobutylyl chloride in 2 ml of dry dichloromethane in 5 minutes. The reaction was carried out at room temperature for additional 1 hour with stirring. After the reaction, the reaction solution was well washed with water, dried over anhydrous magnesium sulfate, and subjected to removal of the solvent by distillation. The resulting residue was purified by column chromatograph (filler: Wakogel C-300, eluent: a mixed solvent of n-hexane and ethyl acetate) to give pale yellow crystals of N-(4-isobutylyloxyphenyl)-2-[(E)-1-(2-methyl-5-phenyl- 3 -thienyl)ethylidene]- 3 -isopropylidenesuccinimide in yield of 70.0%.

m.p.: 158°–159° C.
MS: 499 (M+)
Elementary analysis:

|           | C     | H    | N    |
|-----------|-------|------|------|
| Calcd. (%) | 72.13 | 5.85 | 2.81 |
| Found (%)  | 72.36 | 5.93 | 2.82 |

IR (KBr) cm$^{-1}$: 2800–3000 (CH$_2$, CH$_3$), 1740, 1720, 1700 (NCO, COO), 1500 (phenyl), 1370, 1200, 1160 (CH$_3$), 770, 700 (thienyl)

REFERENCE EXAMPLE 8

Stability test of color formed for fulgimide derivatives

Storing stability of color formed by exposing the polymer type fulgimide derivative obtained in Example 24 and the fulgimide derivative obtained in Reference Example 7 to ultraviolet light was examined as follows.

Preparation of Samples

Sample No. 1:
A solution obtained by dissolving 1 part of the polymer type fulgimide derivative obtained in Example 24 in 10 parts of a mixed solvent of acetone and cyclohexane (1:1 by weight) was coated on a glass plate in an amount of 5 ml using a bar coater, followed by drying to form a film (Sample No. 1).

Sample No. 2:
A solution obtained by dissolving 0.1 part of the fulgimide derivative obtained in Reference Example 7 and 0.9 part of poly(methyl methacrylate) (average molecular weight: 12,000, mfd. by Aldrich Chemical Co., Inc.) in 10 parts of a mixed solvent of acetone and cyclohexane (1:1 weight ratio) was coated on a glass plate in an amount of 5 ml using a bar coater, followed by drying to form a film (Sample No. 2).

Storing Stability Test of Color Formed

The above-mentioned samples were exposed to ultraviolet light of near 360 nm [light source: 500 W ultrahigh pressure mercury lamp (mfd. by Ushio Inc.), filter: IRA-25S and UV-D36C (mfd. by Toshiba Glass Co., Ltd.)] for 2 minutes for color formation, followed by storing in the dark (temperature: 80° C.) for predetermined times as listed in Table 1.

After storing for a predetermined time, a colored sample was subjected to measurement of absorbance at 550 nm. The storing stability of color formed was obtained from the following equation:

$$\text{Storing stability of color formed (\%)} = \frac{(A_0 - A)}{A_0} \times 100$$

wherein $A_0$ is an absorbance of a sample at 550 nm immediately after irradiation of ultraviolet light; and A is an absorbance of a sample at 550 nm after stored for a predetermined fine after irradiation of ultraviolet light.

Results

The results are shown in Table 1.

TABLE 1

| Sample No. | Storing stability (%) | |
|---|---|---|
| | 120 hrs | 192 hrs |
| 1 | 4.8 | 8.9 |
| 2 | 6.7 | 16.7 |

As is clear from the results of Table 1, the storing stability of color formed of the polymer obtained from a fulgimide derivative having a vinyl group of the present invention is significantly higher than that of a simple mixture of a fulgimide derivative and the polymer.

As mentioned above, the fulgimide derivatives of the present invention have photochromic activity and useful as recording and memory materials, copying materials, printed photosensitive bodies, photosensitive materials for laser, photosensitive materials for photo-composing, photosensitive materials for display, etc. by themselves. Further, since the fulgimide derivatives of the present invention have a reactive functional group in their molecules, they can be effectively used as starting materials for synthesizing fulgimide derivatives having various useful functional groups introduced therein. In addition, fulgimide derivatives of the present invention having a vinyl group can be used for producing polymers and copolymers with suitable other monomers, having photochromic activity.

What is claimed is:

1. A fulgimide derivative of the formula:

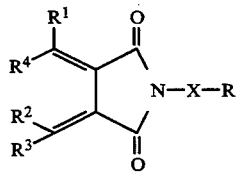

wherein $R^1$, $R^2$ and $R^3$ are independently a hydrogen atom, a halogen atom, a $C_{1-4}$ alkyl group which may be substituted with one or more hydroxyl groups, $C_{1-4}$ alkoxyl groups or halogen atoms, a $C_{1-4}$ alkoxy group, a $C_{3-6}$ cycloalkyl group, a $C_6$-$C_{12}$ aryl group, a $C_{7-17}$ aralkyl group or a $C_{6-16}$ aryloxy group, and $R^2$ and $R^3$ may be bonded to each other to form an adamantyl or a norbornyl group; $R^4$ is a group of the formula:

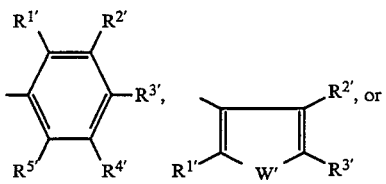

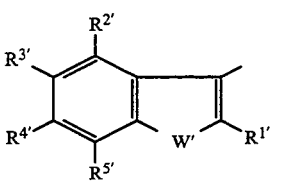

wherein $R^{1'}$ is a hydrogen atom, a halogen atom, a $C_{1-4}$ alkyl group or a $C_{1-4}$ alkoxy group; $R^{2'}$, $R^{3'}$, $R^{4'}$, and $R^{5'}$ are independently a hydrogen atom, a $C_{1-4}$ alkyl group, $C_{1-4}$ alkoxy group, a $C_{6-12}$ aryl group, a $C_{7-17}$ aralkyl group, a $C_{6-16}$ aryloxy group or a halogen atom; W' is an oxygen atom, a sulfur atom, a selenium atom, or $>N-R^{6'}$; $R^{6'}$ is a $C_{1-4}$ alkyl group; X is an arylene group, a group of the formula

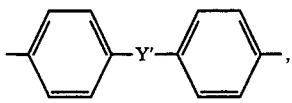

wherein Y' is an alkylene group; or a group of the formula:

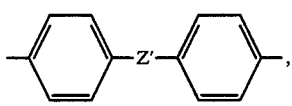

wherein Z' is an oxygen atom, a sulfur atom or a sulfonyl group; R is an amino group which may be substituted with one or more $C_{1-4}$ alkyl groups, hydroxy alkyl groups, and sulfoalkyl groups and acyl groups having 2 to 16 carbon atoms, a hydroxyl group, a formyl group, a carboxyl group, a sulfonic acid group, an acetal group, a halogen atom,

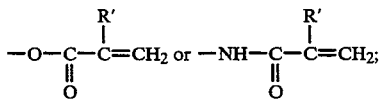

R' is a hydrogen atom or a $C_{1-4}$ alkyl group.

2. A fulgimide derivative according to claim 1, wherein R in the formula is an amino group which may be substituted with one or more $C_{1-4}$ alkyl groups, hydroxy alkyl groups, sulfoalkyl groups or a $C_{2-16}$ acyl groups, a hydroxyl group, a formyl group, a carboxyl group, a sulfonic acid group, an acetal group or a halogen atom.

3. A fulgimide derivative according to claim 1, wherein R in the formula is a group of the formula:

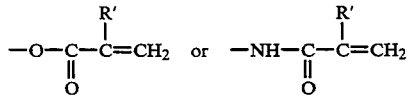

wherein R' is a hydrogen atom or an alkyl group.

4. A fulgimide derivative according to claim 1, which is represented by the formula:

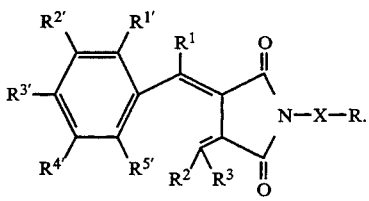

5. A fulgimide derivative according to claim 1, which is represented by the formula:

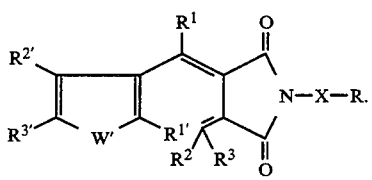

6. A fulgimide derivative of the formula:

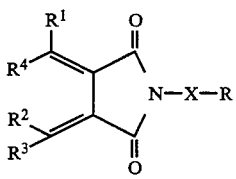

wherein $R^1$, $R^2$ and $R^3$ are independently a hydrogen atom, a halogen atom, a $C_{1-4}$ alkyl group which may be substituted with one or more hydroxyl groups, $C_{1-4}$ alkoxy groups or halogen atoms; a $C_{1-4}$ alkoxy group, a $C_{3-6}$ cycloalkyl group, a $C_{6-12}$ aryl group, a $C_{7-17}$ aralkyl group or a $C_{6-16}$ aryloxy group, and $R^2$ and $R^3$ may be bonded to each other to form an adamantyl or norbornyl group; $R^4$ is a group of the formula:

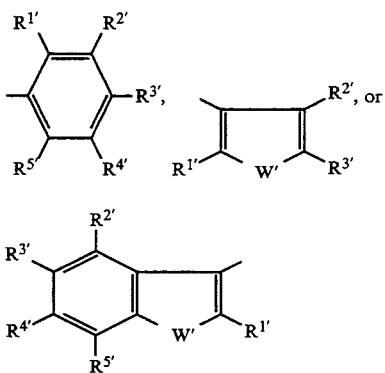

wherein $R^{1'}$ is a hydrogen atom, a halogen atom, a $C_{1-4}$ alkyl group or a $C_{1-4}$ alkoxy group; $R^{2'}$, $R^{3'}$, $R^{4'}$, and $R^{5'}$ are independently a hydrogen atom, a $C_{1-4}$ alkyl group, a $C_{1-4}$ alkoxy group, a $C_{6-12}$ aryl group, a $C_{7-17}$ aralkyl group, a $C_{6-16}$ aryloxy group or a halogen atom; W' is an oxygen atom, a sulfur atom, a selenium atom, or $>N-R^{6'}$; $R^{6'}$ is $C_{1-4}$ alkyl group; X is an alkylene group; and R is a hydroxyl group, a formyl group, a carboxyl group, a sulfonic acid group, an acetal group, a halogen atom, or an amino group which may be substituted with one or more $C_{1-4}$ alkyl groups, hydroxyalkyl groups, sulfoalkyl groups, or acyl groups having 2-16 carbon atoms.

7. A fulgimide derivative according to claim 6, which is represented by the formula:

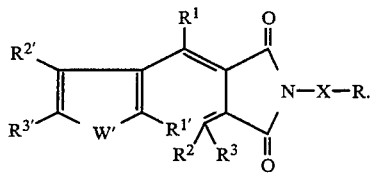

8. A fulgimide derivative according to claim 1, which is represented by the formula:

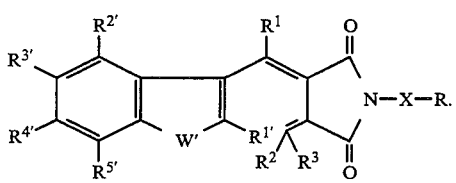

9. A fulgimide derivative according to claim 8, wherein X is

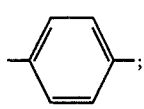

R is an amino group, a hydroxyl group, or a group of the formula:

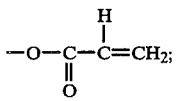

$R^1$ through $R^3$ are methyl groups; W' is $>N-CH_3$; $R^{1'}$ is a methyl group; and $R^{2'}$ through $R^{5'}$ are independently a hydrogen atom or a $C_{1-4}$ alkoxy group.

10. A fulgimide derivative according to claim 8, wherein $R^1$, $R^2$ and $R^3$ are independently a hydrogen atom, a halogen atom, a $C_{1-4}$ alkyl group which may be substituted with one or more hydroxyl groups, $C_{1-4}$ alkoxyl groups or halogen atoms; a $C_{1-4}$ alkoxy group, a $C_{3-6}$ cycloalkyl group, a $C_{6-12}$ aryl group, a $C_{7-17}$ aralkyl group or a $C_{6-16}$ aryloxy group; $R^{2'}$, $R^{3'}$, $R^{4'}$, and $R^{5'}$ are independently a hydrogen atom, a $C_{1-4}$ alkyl group, a $C_{1-4}$ alkoxy group, a $C_{6-12}$ aryl group, a $C_{7-17}$ aralkyl group, a $C_{6-16}$ aryloxy group or a halogen atom; W' is an oxygen atom, a sulfur atom, a selenium atom, or $>N-R^{6'}$; $R^{6'}$ is a $C_{1-4}$ alkyl group; X is an arylene group, a group of the formula

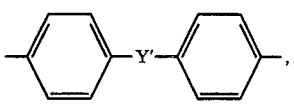

wherein Y' is an alkylene group; or a group of the formula:

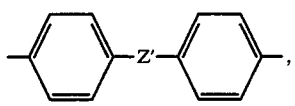

wherein Z' is an oxygen atom, a sulfur atom or a sulfonyl group; R is an amino group which may be substituted with one or more $C_{1-4}$ alkyl groups, hydroxy alkyl groups, sulfoalkyl groups and acyl groups having 2-16 carbon atoms, a hydroxyl group, a formyl group, a carboxyl group, a sulfonic acid group, an acetal group, a halogen atom

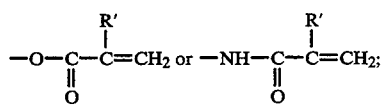

R' is a hydrogen atom or $C_{1-4}$ alkyl group.

11. A fulgimide derivative according to claim 8, wherein W' is >N-alkyl and $R^1$, $R^2$, $R^3$ and $R^{1'}$ are alkyl groups.

12. A fulgimide derivative according to claim 8, wherein W' is oxygen, and $R^1$, $R^2$, $R^3$ and $R^{1'}$ are alkyl groups.

13. A fulgimide derivative according to claim 8, wherein W' is sulfur, and $R^1$, $R^2$, $R^3$ and $R^{1'}$ are alkyl groups.

14. A fulgimide of the formula:

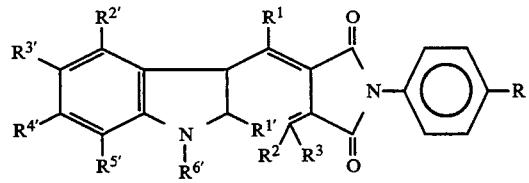

wherein R is a hydroxy alkyl group, a formyl group, a carboxyl group, a sulfonic acid group, an acetal group, a halogen atom,

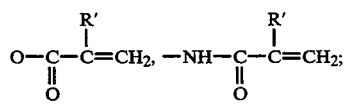

an amino group which may be substituted with one or more $C_{1-4}$ alkyl groups, hydroxyl groups, sulfoalkyl groups, and acyl groups having 2-16 carbon atoms;

R' is a hydrogen atom or a $C_{1-4}$ alkyl group;

$R^1$, $R^2$, $R^3$, $R^{1'}$ and $R^{6'}$ are $C_{1-4}$ alkyl groups; and $R^{2'}$, $R^{3'}$, and $R^{5'}$ are independently a hydrogen atom, a $C_{1-4}$ alkyl group, a $C_{1-4}$ alkoxy group, a $C_{6-12}$ aryl group, a $C_{7-17}$ aralkyl group, a $C_{6-16}$ aryloxy group or a halogen atom.

15. A mineral acid or organic acid salt of a fulgimide derivative of the formula:

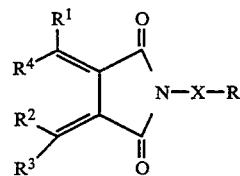

(I)

wherein $R^1$, $R^2$ and $R^3$ are independently a hydrogen atom, a halogen atom, a $C_{1-4}$ alkyl group which may be substituted with one or more hydroxyl groups, $C_{1-4}$ alkoxy groups or halogen atoms; a $C_{1-4}$ alkoxy group, a $C_{3-6}$ cycloalkyl group, a $C_{6-12}$ aryl group, a $C_{7-17}$ aralkyl group or a $C_{6-16}$ aryloxy group, and $R_2$ and $R^3$ may be bonded to each other to form an adamantyl or norbornyl group; $R^4$ is a group of the formula:

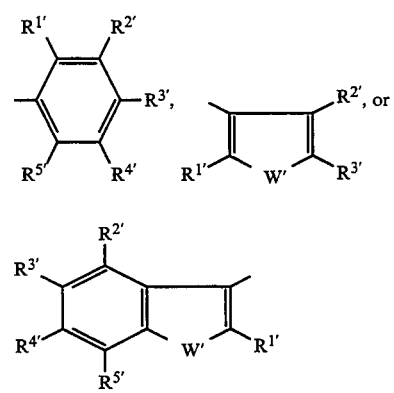

wherein $R^{1'}$ is a hydrogen atom, a halogen atom, a $C_{1-4}$ alkyl group or a $C_{1-4}$ alkoxy group; $R^{2'}$, $R^{3'}$, $R^{4'}$, and $R^{5'}$ are independently a hydrogen atom, a $C_{1-4}$ alkyl group, a $C_{1-4}$ alkoxy group, a $C_{6-12}$ aryl group, a $C_{7-17}$ aralkyl group, a $C_{6-16}$ aryloxy group or a halogen atom, W' is an oxygen atom, a sulfur atom, a selenium atom or >N-$R^{6'}$; $R^{6'}$ is a $C_{1-4}$ alkyl group, X is an arylene group, a group of the formula

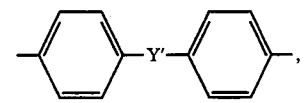

wherein Y' is an alkylene group, or a group of the formula:

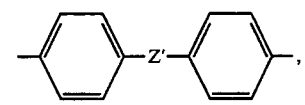

wherein Z' is an oxygen atom, a sulfur atom or a sulfonyl group; and R is an amino group which may be substituted with one or more $C_{1-4}$ alkyl groups, hydroxyalkyl groups, sulfoalkyl groups or acyl groups having 2 to 16 carbon atoms.

16. An alkali metal or ammonium salt of a fulgimide derivative of the formula:

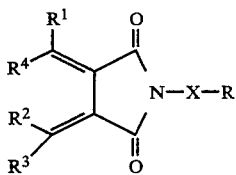
(I)

wherein $R^1$, $R^2$ and $R^3$ are independently a hydrogen atom, a halogen atom, a $C_{1-4}$ alkyl group which may be substituted with one or more hydroxyl groups, $C_{1-4}$ alkoxy groups or halogen atoms; a $C_{1-4}$ alkoxy group, a $C_{3-6}$ cycloalkyl group, a $C_{6-12}$ aryl group, a $C_{7-17}$ aralkyl group or $C_{6-16}$ aryloxy group, and $R_2$ and $R^3$ may be bonded to each other to form an adamantyl group; $R^4$ is a group of the formula:

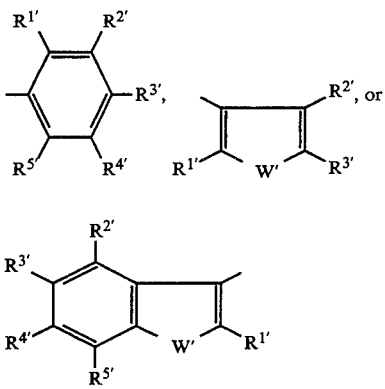

wherein $R^{1'}$ is a hydrogen atom, a halogen atom, a $C_{1-4}$ akyl group or a $C_{1-4}$ alkoxy group; $R^{2'}$, $R^{3'}$, $R^{4'}$, and $R^{5'}$ are independently a hydrogen atom, a $C_{1-4}$ alkyl group, a $C_{1-4}$ alkoxy group, a $C_{6-12}$ aryl group, a $C_{7-17}$ aralkyl group, a $C_{6-16}$ aryloxy group or a halogen atom, W' is an oxygen atom, a sulfur atom, a selenium atom or $>N-R^{6'}$; $R^{6'}$ is a $C_{1-4}$ alkyl group, X is an arylene group, a group of the formula

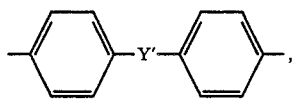

wherein Y' is an alkylene group, or a group of the formula:

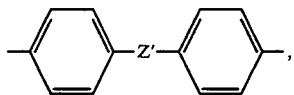

wherein Z' is an oxygen atom, a sulfur atom or a sulfonyl group; and R is a carboxyl group or a sulfonic acid group.

17. A mineral acid or organic acid salt of a fulgimide derivative of the formula:

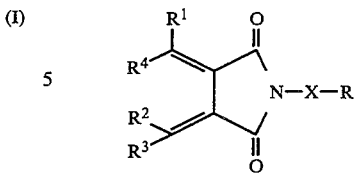

wherein $R^1$, $R^2$ and $R^3$ are independently a hydrogen atom, a halogen atom, a $C_{1-4}$ alkyl group which may be substituted with one or more hydroxyl groups, $C_{1-4}$ alkoxy groups or halogen atoms; a $C_{1-4}$ alkoxy group, a $C_{3-6}$ cycloalkyl group, a $C_{6-12}$ aryl group, a $C_{7-17}$ aralkyl group or a $C_{6-16}$ aryloxy group, and $R_2$ and $R^3$ may be bonded to each other to form an adamantyl group or norbornyl group; $R^4$ is a group of the formula:

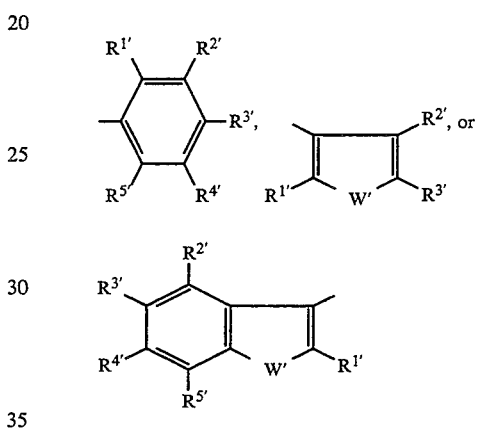

wherein $R^{1'}$ is a hydrogen atom, a halogen atom, a $C_{1-4}$ alkyl group or a $C_{1-4}$ alkoxy group; $R^{2'}$, $R^{3'}$, $R^{4'}$, and $R^{5'}$ are independently a hydrogen atom, a $C_{1-4}$ alkyl group, a $C_{1-4}$ alkoxy group, a $C_{6-12}$ aryl group, a $C_{7-17}$ aralkyl group, a $C_{6-16}$ aryloxy group or a halogen atom, W' is an oxygen atom, a sulfur atom, a selenium atom or $>N-R^{6'}$; $R^{6'}$ is a $C_{1-4}$ alkyl group, X is an alkylene group; and R is an amino acid which may be substituted with one or more $C_{1-4}$ alkyl groups, hydroxyalkyl groups, sulfoalkyl groups or acyl groups having 2–16 carbon atoms.

18. An alkali metal or ammonium salt of a fulgimide derivative of the formula:

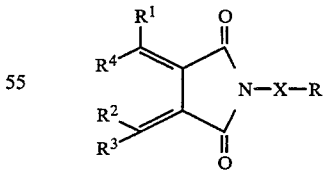

wherein $R^1$, $R^2$ and $R^3$ are independently a hydrogen atom, a halogen atom, a $C_{1-4}$ alkyl group which may be substituted with one or more hydroxyl groups, $C_{1-4}$ alkoxy groups or halogen atoms; a $C_{1-4}$ alkoxy group, a $C_{3-6}$ cycloalkyl group, a $C_{6-12}$ aryl group, a $C_{7-17}$ aralkyl group or a $C_{6-16}$ aryloxy group, and $R_2$ and $R^3$ may be bonded to each other to form an adamantyl group or norbornyl group; $R^4$ is a group of the formula:

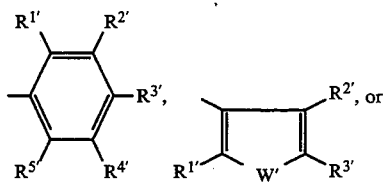

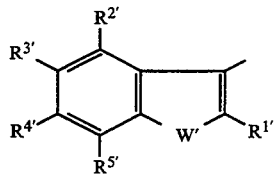

wherein $R^{1'}$ is a hydrogen atom, a halogen atom, a $C_{1-4}$ alkyl group or a $C_{1-4}$ alkoxy group; $R^{2'}$, $R^{3'}$, $R^{4'}$ and $R^{5'}$ are independently a hydrogen atom, a $C_{1-4}$ alkyl group, a $C_{1-4}$ alkoxy group, a $C_{6-12}$ aryl group, a $C_{7-17}$ aralkyl group, a $C_{6-16}$ aryloxy group or a halogen atom, W' is an oxygen atom, a sulfur atom, a selenium atom or $>N-R^{6'}$; $R^{6'}$ is a $C_{1-4}$ alkyl group, X is an alkylene group; and R is a carboxyl group or a sulfonic acid group.

19. A fulgimide derivative which is represented by the formula:

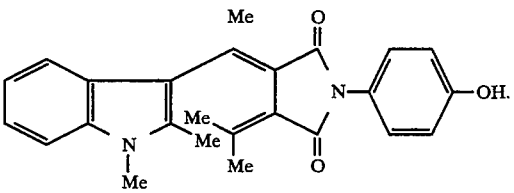

* * * * *